United States Patent
Satish et al.

(10) Patent No.: US 9,773,320 B2
(45) Date of Patent: Sep. 26, 2017

(54) METHOD FOR ESTIMATING A QUANTITY OF A BLOOD COMPONENT IN A FLUID CANISTER

(71) Applicant: Gauss Surgical, Inc., Los Altos, CA (US)

(72) Inventors: Siddarth Satish, Los Altos, CA (US); Kevin J. Miller, Los Altos, CA (US); Yaser Yacoob, Los Altos, CA (US); Andrew T. Hosford, Los Altos, CA (US); Charlie Carroll, Los Altos, CA (US); Grant Kadokura, Palo Alto, CA (US); Tyler Stout, Palo Alto, CA (US); Juan Carlos Aragon, Palo Alto, CA (US); Michael Hsieh, Los Altos, CA (US)

(73) Assignee: Gauss Surgical, Inc., Los Altos, CA (US)

( * ) Notice: Subject to any disclaimer, the term of this patent is extended or adjusted under 35 U.S.C. 154(b) by 278 days.

(21) Appl. No.: 14/687,862

(22) Filed: Apr. 15, 2015

(65) Prior Publication Data
US 2015/0294461 A1 Oct. 15, 2015

Related U.S. Application Data

(60) Provisional application No. 61/980,027, filed on Apr. 15, 2014, provisional application No. 62/080,927, filed on Nov. 17, 2014.

(51) Int. Cl.
*G06K 9/00* (2006.01)
*G06T 7/40* (2017.01)
(Continued)

(52) U.S. Cl.
CPC ............. *G06T 7/408* (2013.01); *G01N 33/49* (2013.01); *G06T 7/0014* (2013.01); *G06T 7/194* (2017.01);
(Continued)

(58) Field of Classification Search
CPC .......... G06T 7/408; G06T 7/194; G06T 7/90; G06T 7/0014; G06T 2207/10152;
(Continued)

(56) References Cited

U.S. PATENT DOCUMENTS

| | | | |
|---|---|---|---|
| 2,707,955 A | 5/1955 | Borden | |
| 3,182,252 A | 5/1965 | Den Berg | |

(Continued)

FOREIGN PATENT DOCUMENTS

| | | |
|---|---|---|
| CA | 2870635 A1 | 10/2013 |
| CN | 101505813 | 8/2009 |

(Continued)

OTHER PUBLICATIONS

Sant, et al. "Exsanguinated Blood Volume Estimation Using Fractal Analysis of Digital Images." Journal of Forensic Sciences 57.3 (2012): 610-17. Print.
(Continued)

*Primary Examiner* — Jonathan S Lee
(74) *Attorney, Agent, or Firm* — Cooley LLP

(57) ABSTRACT

A method and system for assessing an amount of a blood component of a volume of fluid within a canister, the method comprising: receiving an image of the canister generated by the image acquisition device; selecting a first region of the image exhibiting substantially uniform color, wherein the first region of the image corresponds to a layer of fluid situated between a wall of the canister and a first feature of an insert retained in position within the canister; determining a color parameter representative of the first region; deter-
(Continued)

mining a concentration of a blood component within the canister, based upon the color parameter; upon determining the volume of fluid of fluid within the canister, generating an analysis informative of an amount of the blood component within the canister; and providing information derived from the analysis to an entity associated with an individual from whom the volume of fluid originated.

22 Claims, 13 Drawing Sheets

(51) Int. Cl.
    *G01N 33/49*     (2006.01)
    *G06T 7/00*     (2017.01)
    *G06T 7/90*     (2017.01)
    *G06T 7/194*     (2017.01)

(52) U.S. Cl.
    CPC ...... *G06T 7/90* (2017.01); *G06T 2207/10152* (2013.01); *G06T 2207/20072* (2013.01); *G06T 2207/20076* (2013.01); *G06T 2207/30024* (2013.01)

(58) Field of Classification Search
    CPC . G06T 2207/20072; G06T 2207/20076; G06T 2207/30024; G01N 33/49
    See application file for complete search history.

(56) References Cited

U.S. PATENT DOCUMENTS

| | | |
|---|---|---|
| 3,199,507 A | 8/1965 | Kamm |
| 3,367,431 A | 2/1968 | Prindle Baker |
| 3,646,938 A | 3/1972 | Haswell |
| 3,832,135 A | 8/1974 | Chlupsa et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |
| 4,402,373 A | 9/1983 | Comeau |
| 4,422,548 A | 12/1983 | Cheesman et al. |
| 4,429,789 A | 2/1984 | Puckett |
| 4,512,431 A | 4/1985 | Bloomfield |
| 4,562,842 A | 1/1986 | Morfeld et al. |
| 4,583,546 A | 4/1986 | Garde |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,128,036 A | 7/1992 | Svensson |
| 5,132,087 A | 7/1992 | Manion et al. |
| 5,190,059 A | 3/1993 | Fabian et al. |
| 5,231,032 A | 7/1993 | Ludvigsen |
| 5,236,664 A | 8/1993 | Ludvigsen |
| 5,285,682 A | 2/1994 | Micklish |
| 5,458,566 A | 10/1995 | Herrig et al. |
| 5,492,537 A | 2/1996 | Vancaillie |
| 5,522,805 A | 6/1996 | Vancaillie et al. |
| 5,568,262 A | 10/1996 | LaChapelle et al. |
| 5,595,456 A | 1/1997 | Berg et al. |
| 5,629,498 A | 5/1997 | Pollock et al. |
| 5,633,166 A | 5/1997 | Westgard et al. |
| 5,646,788 A | 7/1997 | Bietry |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,971,948 A | 10/1999 | Pages et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,641,039 B2 | 11/2003 | Southard |
| 6,704,500 B2 | 3/2004 | Takematsu |
| 6,728,561 B2 | 4/2004 | Smith et al. |
| 6,730,054 B2 | 5/2004 | Pierce et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | McCall |
| D611,731 S | 3/2010 | Levine |
| 7,670,289 B1 | 3/2010 | McCall |
| 7,703,674 B2 | 4/2010 | Stewart et al. |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,279,068 B2 | 10/2012 | Morris et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,797,439 B1 | 8/2014 | Coley et al. |
| 8,897,523 B2 | 11/2014 | Satish et al. |
| 8,983,167 B2 | 3/2015 | Satish et al. |
| 9,047,663 B2 | 6/2015 | Satish et al. |
| 9,171,368 B2 | 10/2015 | Satish et al. |
| 9,595,104 B2 | 3/2017 | Satish et al. |
| 9,652,655 B2 | 5/2017 | Satish et al. |
| 2003/0069509 A1* | 4/2003 | Matzinger .............. G01N 33/80 600/504 |
| 2003/0095197 A1 | 5/2003 | Wheeler et al. |
| 2003/0130596 A1 | 7/2003 | Von Der Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2006/0058593 A1 | 3/2006 | Drinan et al. |
| 2006/0178578 A1 | 8/2006 | Tribble et al. |
| 2006/0224086 A1 | 10/2006 | Harty |
| 2006/0241453 A1 | 10/2006 | Nguyen-Dinh et al. |
| 2007/0004959 A1 | 1/2007 | Carrier et al. |
| 2007/0008622 A1 | 1/2007 | Sommer |
| 2007/0287182 A1 | 12/2007 | Morris et al. |

(56) References Cited

U.S. PATENT DOCUMENTS

| | | | |
|---|---|---|---|
| 2008/0029416 | A1 | 2/2008 | Paxton |
| 2008/0030303 | A1 | 2/2008 | Kobren et al. |
| 2008/0045845 | A1 | 2/2008 | Pfeiffer et al. |
| 2008/0194906 | A1 | 8/2008 | Mahony et al. |
| 2009/0076470 | A1 | 3/2009 | Ryan |
| 2009/0257632 | A1* | 10/2009 | Lalpuria ............... G06T 7/0012 382/128 |
| 2009/0310123 | A1 | 12/2009 | Thomson |
| 2009/0317002 | A1 | 12/2009 | Dein |
| 2010/0003714 | A1 | 1/2010 | Bachur, Jr. et al. |
| 2010/0007727 | A1 | 1/2010 | Torre-Bueno |
| 2010/0025336 | A1 | 2/2010 | Carter et al. |
| 2010/0027868 | A1 | 2/2010 | Kosaka et al. |
| 2010/0066996 | A1 | 3/2010 | Kosaka et al. |
| 2010/0087770 | A1 | 4/2010 | Bock et al. |
| 2010/0280117 | A1 | 11/2010 | Patrick et al. |
| 2011/0192745 | A1 | 8/2011 | Min |
| 2011/0196321 | A1 | 8/2011 | Wudyka |
| 2011/0200239 | A1 | 8/2011 | Levine et al. |
| 2011/0275957 | A1 | 11/2011 | Bhandari |
| 2011/0305376 | A1 | 12/2011 | Neff |
| 2011/0316973 | A1 | 12/2011 | Miller et al. |
| 2012/0000297 | A1 | 1/2012 | Hashizume et al. |
| 2012/0065482 | A1 | 3/2012 | Robinson et al. |
| 2012/0210778 | A1 | 8/2012 | Palmer et al. |
| 2012/0257188 | A1 | 10/2012 | Yan et al. |
| 2012/0262704 | A1 | 10/2012 | Zahniser et al. |
| 2012/0271170 | A1 | 10/2012 | Emelianov et al. |
| 2012/0309636 | A1 | 12/2012 | Gibbons et al. |
| 2013/0010094 | A1 | 1/2013 | Satish et al. |
| 2013/0170729 | A1 | 7/2013 | Wardlaw et al. |
| 2013/0245599 | A1 | 9/2013 | Williams et al. |
| 2013/0301901 | A1 | 11/2013 | Satish et al. |
| 2013/0303870 | A1 | 11/2013 | Satish et al. |
| 2013/0308852 | A1 | 11/2013 | Hamsici et al. |
| 2014/0079297 | A1 | 3/2014 | Tadayon et al. |
| 2014/0128838 | A1 | 5/2014 | Satish et al. |
| 2014/0207091 | A1 | 7/2014 | Heagle et al. |
| 2014/0330094 | A1 | 11/2014 | Pacione et al. |
| 2015/0310634 | A1* | 10/2015 | Babcock ................ G01N 33/18 382/165 |
| 2015/0354780 | A1 | 12/2015 | Wang |
| 2016/0027173 | A1 | 1/2016 | Satish et al. |
| 2016/0123998 | A1* | 5/2016 | MacIntyre ......... A61B 5/02042 436/66 |
| 2016/0331282 | A1 | 11/2016 | Satish et al. |
| 2017/0011276 | A1* | 1/2017 | Mehring ............... G06K 9/4652 |
| 2017/0023446 | A1* | 1/2017 | Rietveld .......... A61B 5/150358 |

FOREIGN PATENT DOCUMENTS

| | | |
|---|---|---|
| JP | S-59-161801 U | 10/1984 |
| JP | S-62-144652 A | 6/1987 |
| JP | H06510210 A | 11/1994 |
| JP | H-11-37845 A | 2/1999 |
| JP | 2002-331031 A | 11/2002 |
| JP | 2003-075436 A | 3/2003 |
| JP | 2005-052288 A | 3/2005 |
| JP | 3701031 B2 | 9/2005 |
| JP | 2006-280445 A | 10/2006 |
| JP | 2008-055142 A | 3/2008 |
| JP | 2011-515681 A | 5/2011 |
| WO | 9217787 A1 | 10/1992 |
| WO | 9639927 A1 | 12/1996 |
| WO | WO-97/10856 A1 | 3/1997 |
| WO | WO-2009/117652 A1 | 9/2009 |
| WO | 2011019576 A1 | 2/2011 |
| WO | 2013009709 A | 1/2013 |
| WO | 2013172874 A | 11/2013 |
| WO | 2013173356 A | 11/2013 |
| WO | WO-2015/161003 A1 | 10/2015 |
| WO | WO-2016/187071 A1 | 11/2016 |

OTHER PUBLICATIONS

Bellad, et al. "Standardized Visual Estimation of Blood Loss during Vaginal Delivery with its Correlation Hematocrit Changes—A Descriptive Study." South Asian Federation of Obstetrics and Gynecology 1.1 (2009): 29-34. Web.

Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>.

Kamiyoshihara, M. et al. The Utility of an Autologous Blood Salvage System in Emergency Thoracotomy for a emothorax After Chest Trauma. Gen. Thorac. Cargiovasc. Surg. (2008); vol. 56, p. 222.

Pogorelc, D. iPads in the OR: New Mobile Platform to Monitor Blood Loss During Surgery. Jun. 6, 2012. <http://medcitynews.com/2012/06/ipads-in-the-or-new-mobile-platform-to-monitor-blood-loss-during-surgery/>.

ACOG (2012). "Optimizing protocols in obstetrics," Series 2, 25 total pages.

Adkins, A.R. et al. (2014). "Accuracy of blood loss estimations among anesthesia providers," *AANA Journal* 82(4):300-306.

Al-Kadri, H.M. et al. (2014). "Effect of education and clinical assessment on the accuracy of post partum blood loss estimation," *BMC Preg. Childbirth* 14:110, 7 total pages.

AWHONN Practice Brief (2014). "Quantification of blood loss: AWHONN practice brief No. 1," *AWHONN* p. 1-3.

Bose, P. et al. (2006). "Improving the accuracy of estimated blood loss at obstetric haemorrhage using clinical reconstructions," *BJOG* 113(8):919-924.

Eipe, N. et al. (2006). "Perioperative blood loss assessment—How accurate?" *Indian J. Anaesth.* 50(1):35-38.

Extended European Search Report dated Apr. 1, 2015, for EP Application No. 12 810 640.8, filed on Jul. 9, 2012, 8 pages.

Extended European Search Report dated Nov. 23, 2015, for EP Application No. 13 790 688.9, filed on May 14, 2013, 9 pages.

Extended European Search Report dated Nov. 17, 2015, for EP Application No. 13 790 449.6, filed on Jan. 10, 2013, 8 pages.

Extended European Search Report dated Nov. 4, 2016, for EP Application No. 16 183 350.4, filed on Jul. 9, 2012, 9 pages.

Final Office Action dated Feb. 12, 2016, for U.S. Appl. No. 13/544,664, filed Jul. 9, 2012, 9 pages.

Final Office Action dated Aug. 26, 2016, for U.S. Appl. No. 13/894,054, filed May 14, 2013, 7 pages.

Final Office Action dated Jul. 26, 2016, for U.S. Appl. No. 14/876,628, filed Oct. 6, 2015, 5 pages.

Habak, P.J. et al. (2016). "A comparison of visual estimate versus calculated estimate of blood loss at vaginal delivery," *British J. Med. Medical Res.* 11(4):1-7.

Holmes, A.A. et al. (2014). "Clinical evaluation of a novel system for monitoring surgical hemoglobin loss," *Anesth. Analg.* 119(3):588-594.

International Search Report dated Sep. 17, 2012, for PCT Application No. PCT/US2012/045969, filed on Jul. 9, 2012, 2 pages.

International Search Report dated Sep. 24, 2013, for PCT Application No. PCT/US2013/040976, filed on May 14, 2013, 2 pages.

International Search Report dated Mar. 26, 2013, for PCT Application No. PCT/US2013/021075, filed on Jan. 10, 2013, 2 pages.

International Search Report dated Jul. 8, 2015, for PCT Application No. PCT/US2015/026042, filed on Apr. 15, 2015, 2 pages.

International Search Report dated Aug. 18, 2016, for PCT Application No. PCT/US2016/032561, filed on May 13, 2016, 2 pages.

International Search Report dated Mar. 8, 2017, for PCT Application No. PCT/US2016/068452, filed on Dec. 22, 2016, 3 pages.

Jones, R. (2015). "Quantitative measurement of blood loss during delivery," *AWHONN* p. S41.

Lyndon, A. et al. (2010). "Blood loss: Clinical techniques for ongoing quantitative measurement," *CMQCC Obstetric Hemorrhage Toolkit*, pp. 1-7.

Lyndon, A. et al. (2015). "Cumulative quantitative assessment of blood loss," *CMQCC Obstetric Hemorrhage Toolkit Version* 2.0, pp. 80-85.

Manikandan, D. et al. (2015). "Measurement of blood loss during adenotonsillectomy in children and factors affecting it," *Case Reports in Clinical Medicine* 4:151-156.

(56) References Cited

OTHER PUBLICATIONS

Merck for Mother's Program (2012). Blood loss measurement: Technology opportunity assessment, 9 total pages.
Non-Final Office Action dated Aug. 13, 2015, for U.S. Appl. No. 13/544,664, filed Jul. 9, 2012, 8 pages.
Non-Final Office Action dated Aug. 2, 2016, for U.S. Appl. No. 13/544,664, filed Jul. 9, 2012, 6 pages.
Non-Final Office Action dated May 9, 2014, for U.S. Appl. No. 13/544,679, filed Jul. 9, 2012, 7 pages.
Non-Final Office Action dated Mar. 30, 2016, for U.S. Appl. No. 13/894,054, filed May 14, 2013, 9 pages.
Non-Final Office Action dated Sep. 5, 2014, for U.S. Appl. No. 13/738,919, filed Jan. 10, 2013, 8 pages.
Non-Final Office Action dated Mar. 20, 2015, for U.S. Appl. No. 14/613,807, filed Feb. 4, 2015, 8 pages.
Non-Final Office Action dated Dec. 15, 2015, for U.S. Appl. No. 14/876,628, filed Oct. 6, 2015, 8 pages.
Non-Final Office Action dated Apr. 20, 2017, for U.S. Appl. No. 13/894,054, filed May 14, 2013, 7 pages.
Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):S54-S59.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Jul. 8, 2015, for PCT Application No. PCT/US2015/026042, filed on Apr. 15, 2015, 4 pages.
Written Opinion of the International Searching Authority dated Aug. 18, 2016, for PCT Application No. PCT/US2016/032561, filed on May 13, 2016, 5 pages.
Written Opinion of the International Searching Authority dated Mar. 8, 2017, for PCT Application No. PCT/US2016/068452, filed on Dec. 22, 2016, 9 pages.
U.S. Appl. No. 15/416,986, filed Jan. 26, 2017, by Satish et al.
U.S. Appl. No. 15/594,017, filed May 12, 2017, by Satish et al.

* cited by examiner

METHOD FOR ESTIMATING A QUANTITY OF A BLOOD COMPONENT IN A FLUID CANISTER

CROSS-REFERENCE TO RELATED APPLICATIONS

This application claims the benefit of U.S. Provisional Application Ser. No. 61/980,027, filed on 15 Apr. 2014, and U.S. Provisional Application Ser. No. 62/080,927, filed on 17 Nov. 2014, which are each incorporated herein in its entirety by this reference. This application is also related to U.S. application Ser. No. 14/687,842 filed on 15 Apr. 2015, which is also incorporated herein in its entirety by this reference.

TECHNICAL FIELD

This invention relates generally to the surgical field, and more specifically to a new and useful method for estimating a quantity of a blood component in a canister for use in surgical practice.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method and Applications

Figure 1A:
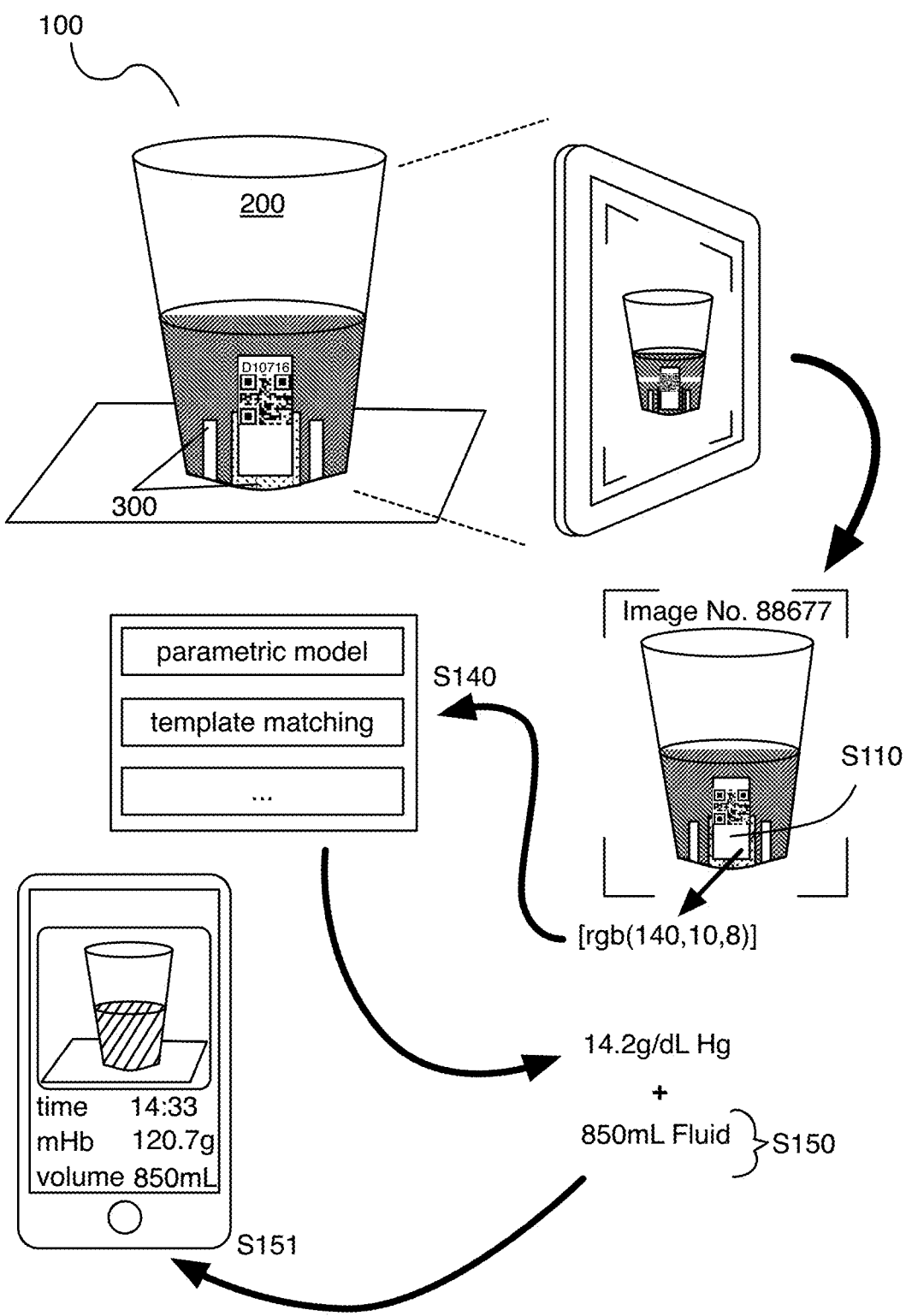
FIGS. 1A, 1B, and 1C depict embodiments of a method for estimating a quantity of a blood component in a canister.
Figure 1B:
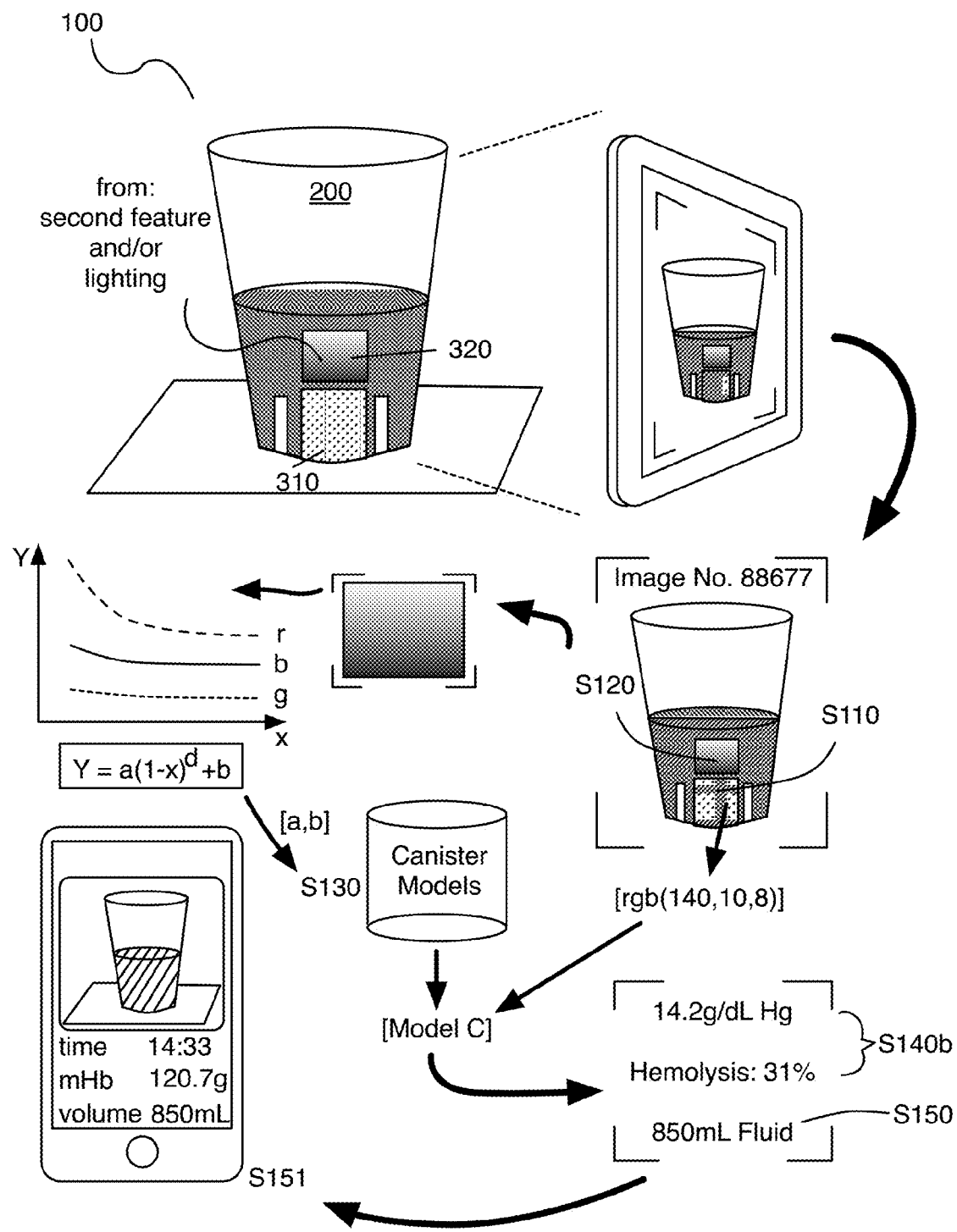
Figure 1C:
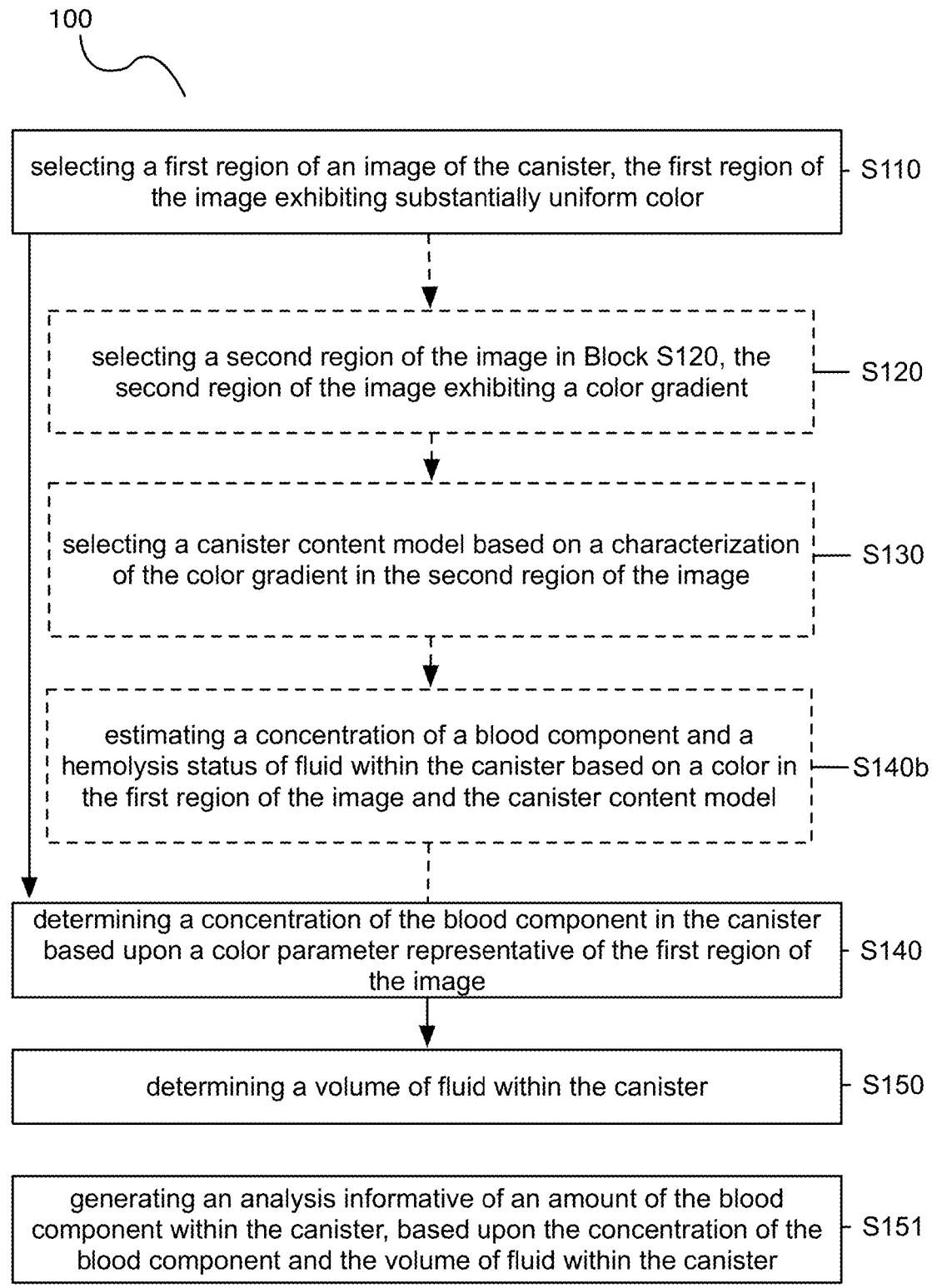

As shown in FIGS. 1A and 1C, a method 100 for estimating a quantity and a quality of a blood component in a canister includes: selecting a first region of an image of the canister S110, the first region of the image exhibiting substantially uniform color; determining a concentration of the blood component in the canister based upon a color parameter representative of the first region of the image S140; determining a volume of fluid within the canister S150; and generating an analysis informative of an amount of the blood component within the canister, based upon the concentration of the blood component and the volume of fluid within the canister S151.

As shown in FIGS. 1B ands 1C, the method 100 can additionally or alternatively include one or more of: selecting a second region of the image S120, the second region of the image exhibiting a color gradient; selecting a canister content model based on a characterization of the color gradient in the second region of the image S130; and estimating a concentration of a blood component and a hemolysis status of fluid within the canister based on a color in the first region of the image and the canister content model S140b. Additionally or alternatively, information from the color gradient can be used as a feature in relation to method blocks for characterization of a fluid component within a container. Additionally or alternatively, information derived from a region of substantially uniform color (or any other suitable feature), as derived from Block S110, can be used in bootstrap aggregation (i.e., bagging), to improve the stability and/or accuracy of one or more characterizations of the method 100.

Generally, the method 100 functions to mitigate effects of color signal saturation associated with high blood component (e.g., hemoglobin) concentrations, which can affect processing of image data in determining a concentration of one or more blood components in the canister. Additionally, the method 100 functions to enable analysis of a state of a blood component present within fluid within the canister, wherein different states of the blood component are observationally distinguishable (e.g., in terms of light absorption behavior, in terms of light scattering behavior, etc.). As such, one or more of: region(s) of substantially uniform color and region(s) exhibiting a color gradient can be used and/or combined to provide features for characterization of a fluid component within a container. Additionally or alternatively, one or more of: region(s) of substantially uniform color and region(s) exhibiting a color gradient can be used and/or combined in bootstrap aggregation (i.e., bagging), to improve the stability and/or accuracy of one or more characterizations of the method 100. In one application, the method 100 can enable analysis of a state of hemolysis of blood within the canister, whereby lysed red blood cells result in a concentration of free hemoglobin within the canister, and wherein free/supernatant hemoglobin has different absorption and scattering properties than intracellular hemoglobin.

As such, the method 100 can implement machine vision to determine both a content of a blood component within a fluid canister and a quality of the blood component in the canister. Additionally, expanded variations of the method 100 can identify and characterize a color gradient in a portion of the image corresponding to fluid in the canister, by incorporating one or more blocks that select a particular model, algorithm, or template image set compatible with the color gradient; pass a substantially uniform color in another region of the image into the particular model, algorithm, or template image set; and generate an estimate of the concentration of a blood component (e.g., hemoglobin) in the canister and an estimate of the quality of the fluid (e.g., in terms of a hemolysis metric, in terms of a ratio of intracellular hemoglobin to supernatant hemoglobin).

Alternatively, the method 100 can identify and characterize a substantially uniform color in one region of the image of the canister; select a particular model, algorithm, or template image set compatible with the uniform color; and then pass a color gradient in another portion of the image into the model, algorithm, or template image set to generate an estimate of the concentration of the blood component in the canister and an estimate of the quality of the fluid. The method 100 can further determine a total volume of fluid within the canister and then combine this total volume with the blood component concentration and the fluid quality into an estimate of an amount of the blood component (e.g., total hemoglobin, free/supernatant hemoglobin, intracellular hemoglobin, red blood cells, whole red blood cells, lysed red blood cells, etc.) in the canister. Such data can thus support or aid a user (e.g., a nurse, an anesthesiologist) in monitoring patient blood loss, in tracking patient euvolemia status, in determining if and when to salvage red blood cells from the canister, in determining when and how much allogeneic blood, autologous blood, or other fluid to transfuse into the patient, and in being informed of patient status in near real time during a patient procedure.

Generally, for a canister (e.g., a surgical suction canister) or other vessel containing bloodied fluid, higher concentrations of hemoglobin—either as free hemoglobin or intracellular hemoglobin—yield fluid with deeper red tint, which can contribute to signal saturation. However, for the same concentration of hemoglobin, a canister containing only whole red blood cells and no free hemoglobin may yield a more opaque fluid of a lighter red tint than a canister containing only free hemoglobin and no whole red blood cells. Furthermore, use of a suction canister to collect blood, irrigant, and other fluids from within or on a patient during a medical procedure—such as through a suction nozzle—may cause an unpredictable portion of collected whole red blood cells to lyse before being deposited into the canister (i.e., as free hemoglobin and broken red blood cell walls). Furthermore, various diseases and bacterial infections may similarly cause intracorporeal red blood cells to lyse at a rate that is not easily modeled across a patient population. Because the proportion of collected red blood cells that remain whole and the proportion of red blood cells that are lysed may not be known without centrifuging all or a portion of fluid contained within the canister (or a sample of a patients blood) and because this proportion of free hemoglobin relative to intracellular hemoglobin in the canister may affect a perceived color of the fluid in the canister even amongst canisters with the same hemoglobin concentration, correlating a color of fluid in a canister with a concentration of hemoglobin in the fluid may yield significant estimation error for ratios of lysed and whole red blood cells significantly beyond a modeled or average value. Therefore, the method 100 can identify a color gradient in a region of the image corresponding to fluid in the canister and extrapolate a metric of light absorption (and/or an opacity) of the fluid from this color gradient. By implementation of a model, algorithm, or set of template images, consistent with this light absorption metric, the method 100 can compensate for hemolysis of red blood cells in the canister. Additionally or alternatively, hemolysis of red blood cells, concentrations of free/bound hemoglobin, and any other suitable parameter can be determined or validated based upon user input of a concentration value (e.g., based upon a manually performed analysis of hemolysis). Finally, by passing a color value of another region of the image into the selected model, algorithm, or set of template images, the method 100 can output hemolysis- and concentration-compensated quantitative metrics of the fluid contained in the canister.

Blood components analyzable according to the variations of the method 100 can include one or more of: whole blood, red blood cells, hemoglobin, platelets, plasma, white blood cells, analytes, and any other suitable blood component or combination of blood components. Furthermore, the blood component can comprise any component derived from any of the above blood components (e.g., intracellular content, molecular content, etc.). Still other variations of the method 100 can additionally or alternatively implement similar techniques to estimate a concentration (and an amount) of a non-blood component within the canister, such as saline, ascites, bile, irrigant saliva, gastric fluid, mucus, pleural fluid, interstitial fluid, urine, fecal matter, or any other bodily fluid of a patient.

The canister can be a suction canister implemented in a surgical or other medical, clinical, or hospital setting to collect blood and other bodily fluids. For example, the canister can include a surgical fluid suction canister defining a translucent polymer vessel including a series of horizontal fluid volume indicator markings arranged vertically along a wall of the vessel and visible from outside the container. The canister can alternatively be a blood salvage canister, an intravenous fluid bag, or any other suitable blood- or fluid-bearing container for collecting surgical waste or recovering biological fluid. The fluid canister is also transparent, translucent, or includes a transparent or translucent region along a wall (e.g., vertical wall) of the canister, such that an image of the canister includes sufficient information to enable the method 100 to color match fluid contained in the fluid canister to a color region printed or applied onto the canister and to estimate a concentration of the blood component within the canister accordingly, as described in U.S. application Ser. No. 14/687,842.

The method 100 can therefore be useful in quantifying an amount and/or a concentration of a blood component (e.g., hemoglobin) and/or other fluids (e.g., saline) contained within a fluid canister through non-contact means (i.e., imaging and image processing) and in near real-time, such as during a surgery or other medical event. A patient's blood loss and euvolemia status can thus be tracked according to these data, such as described in U.S. application Ser. No. 14/072,625, entitled "Method for Triggering Blood Salvage" and filed on 5 Nov. 2013, which is incorporated in its entirety by this reference. The method 100 can also implement methods and techniques described in U.S. patent application Ser. No. 13/544,646 entitled "System and Method for Estimating Extracorporeal Blood Volume in a Physical Sample" and filed on 9 Jul. 2012, U.S. application Ser. No. 13/894,054 entitled "System and Methods for Managing Blood Loss of a Patient" and filed on 14 May 2013, and U.S. application Ser. No. 13/738,919 entitled "System and Method for Estimating a Quantity of a Blood Component in a Fluid Canister" and filed on 10 Jan. 2013, which are each incorporated herein in its entirety by this reference. However, the method 100 can be applicable in any other scenario or environment to estimate a concentration and/or amount of a blood component or other fluid or particulate in a vessel.

The method 100 can be implemented by a computing system, examples of which are shown in FIGS. 9-12, as a fluid receiver analyzer that analyzes a photographic image of a canister (and other fluid receivers) to estimate a quantity and/or a quality of a fluid contained therein. The computer system can be cloud-based (e.g., Amazon EC2), a mainframe computer system, a grid-computer system, or any other suitable computer system. For example, the method 100 can be implemented by a handheld (e.g., mobile) computing device, such as smartphone, a digital music player, or a tablet computer executing a native blood component analysis application. For example, an image acquisition module integral with the computing device can capture the image of the fluid canister, and a processor integral with the computing device can implement Blocks of the method to extrapolate the quality of the fluid in the canister from the image. The computing device can additionally or alternatively communicate with a remote server, such as over the Internet via a wireless connection, the server can perform one or more Blocks of the method 100, and one or more outputs of the method 100 can be transmitted from the remote server back to the computing device for further analysis and/or subsequent presentation to a user (e.g., a nurse, an anesthesiologist). The computing device can also include or can be coupled to a digital display, and the method 100 can present information to the user through the display.

Alternatively, the method 100 can be implemented as a standalone blood volume estimation system including a fluid canister, a fluid canister stand, an image acquisition module, a camera stand configured to support a camera of the image acquisition module adjacent the fluid canister, a digital display, a processor configured to perform at least a portion of the method, and/or a communication module configured to communicate with a remote server that performs one or more Blocks of the method 100. In this implementation, the camera can be substantially non-transiently positioned relative to a fluid canister stand such that the camera remains in a suitable position to capture an image of a canister substantially throughout a surgery or other medical event and/or until the canister is full. The blood volume estimation system can thus regularly capture and analyze images of the fluid canister, such as every thirty seconds or every two minutes. The blood volume estimation system can further communicate (e.g., via Bluetooth) with another one or more systems implementing any of the methods described in U.S. application Ser. Nos. 13/544,646, 13/894,054, 13/738,919, and 14/072,625 to form a fluid management system for generating a substantially comprehensive estimate of extracorporeal blood volume, total patient blood loss, patient euvolemia status, etc. However, the method can be implemented in or by any other computer system, computing device, or combination thereof.

Furthermore, variations of the method 100 and system can be adapted to process image data (or other data) derived from any other suitable fluid receiving substrate (e.g., canister, test strip, absorbent pad, surgical textile, sponge, fluid receiving bag, drape, cell salvage system, drain device, etc.) associated with or otherwise coupled to an element configured to provide a region of substantially uniform color and/or an element configured to provide a color gradient, upon reception (e.g., reception into a cavity, reception upon absorption) of a volume of fluid (e.g., urine, saline, ascites, bile, irrigant saliva, gastric fluid, mucus, pleural fluid, interstitial fluid, fecal matter, etc.) at the fluid receiving substrate. As such, variations of the method 100 and insert 300 described below can facilitate mitigation of signal saturation (e.g., in relation to fluids with high concentration of a certain component), in determining a concentration and/or an amount of a fluid component within a volume of fluid received at the fluid receiving substrate.

2. Uniform Color and Color Gradient Regions

Block S110 recites: selecting a first region of an image of the canister, the first region of the image exhibiting substantially uniform color. Generally, Block S110 functions to identify the canister in the image and to select a particular region of the image that exhibits a substantially uniform color (e.g., less than a threshold color change over a particular distance). In Block S110, a single region or multiple regions exhibiting substantially uniform color (e.g., the same color, different colors) can be selected for use in subsequent blocks of the method 100. Block S110 can then include passing this selected region, a mean or median color value of the selected region, or any other feature derived from the selected region to Block S140, which may implement template matching, a regression function or algorithm, or any other suitable model (e.g., a model selected in Block S130) to convert a color parameter in the selected region into an estimated hemoglobin concentration value. Block S110 is preferably performed at a module of a computing system configured to receive data associated with an image of the canister and generated by an image acquisition device (e.g., camera module), wherein the computing system can be implemented in one or more of: a mobile computing device, a remote server, a cloud platform, a personal computer, and any other suitable processing device. In particular, the computing system can implement modules across multiple subsystems; however, the computing system can alternatively be implemented in a single subsystem. Block S110 can, however, alternatively be implemented using any other suitable system.

In Block S110, selecting the first region of the image of the canister is preferably performed automatically at a module of the computing system. As such, in one variation, once an image of the canister is captured, (e.g., as described in U.S. patent application Ser. No. 13/738,919), Block S110 can comprise implementing machine vision techniques to identify the first region in the image, and/or one or more positional features associated with the first region in the image. Block S110 can comprise implementing one or more of: object localization, segmentation (e.g., edge detection, background subtraction, grab-cut-based algorithms, etc.), gauging, clustering, pattern recognition, template matching, feature extraction, descriptor extraction (e.g., extraction of texton maps, color histograms, HOG, SIFT, etc.), feature dimensionality reduction (e.g., PCA, K-Means, linear discriminant analysis, etc.), feature selection, thresholding, positioning, color analysis, parametric regression, non-parametric regression, unsupervised or semi-supervised parametric or non-parametric regression, and any other type of machine learning or machine vision to identify the first region, and/or positional features that can be used to locate the first region of the image. However, Block S110 can alternatively include manually selecting the first region of the image, for instance, based upon a user input at an input module (e.g., touch pad, touch screen, mouse, etc.) in communication with the computing system. As such, a user input that selects the first region and/or indicates a boundary of the first region can alternatively be used in Block S110 to select the first region of the image exhibiting substantially uniform color.

In relation to the first region of the image exhibiting substantially uniform color, the first region of the image is preferably associated with a first feature of an insert retained within or otherwise coupled to the canister, as described in Section 2.2 below. Block S110 can thus include one or more of: retaining an insert within the canister with a first feature of the insert in a set configuration, such that the insert provides a layer of fluid situated between a wall of the canister and the first feature; coupling an insert to the canister with a first feature of the insert in a configuration that contributes to substantially uniform color across the first region of the canister; generating image data of the canister and the first region of the canister, upon imaging the canister with an image acquisition device; and performing any other suitable action that contributes to selection of the first region within the image of the canister.

Additionally or alternatively, the first region of the image can correspond to an antiglare feature of an element applied or otherwise coupled to the canister, as described in U.S. application Ser. No. 14/687,842, wherein an antiglare layer of a color grid element extends beyond the color grid element over a portion of the canister, in order to mitigate glare effects within image data of the canister. As such, variations of Block S110 can include retaining an insert within the canister with the first feature in a set configuration, and providing alignment between an antiglare region of an element applied to the canister and the first feature in the set configuration, thereby defining the first region of the canister. In a specific example, the antiglare layer of the color grid element extends over a portion of the canister and is in alignment with a feature of an insert, within the canister, that provides a layer of fluid between the wall of the canister and the insert (in contributing to uniform color across the first region); however, the first region of the image can be produced and/or detected in any other suitable manner.

As noted above, some variations of the method 100 can include Block S120, which recites: selecting a second region of the image, the second region of the image exhibiting a color gradient. Generally, Block S120 functions to identify a color gradient across a second region of the image corresponding to fluid within the canister, to characterize the gradient, and to pass this characterization of the color gradient to Block S130. Similar to Block S110, Block S120 can include selection of multiple regions of the image, corresponding to multiple color gradients, for subsequent processing in blocks of the method 100. In particular, by identifying and characterizing a color gradient within the image, Block S120 can generate a metric of the absorption of light by the fluid within the canister (and/or an opacity of the fluid within the canister), in association with a color gradient provided across the second region of the canister, which can be used to assess a level of hemolysis in the canister. Additionally or alternatively, a region of uniform characteristics (e.g., color characteristics) in the image can be used to assess a level of hemolysis in the canister. Thus, in a specific application, one or more outputs of Block S120 can be implemented in subsequent Blocks of the method 100 to both estimate a hemolysis level in the canister and to compensate for hemolysis in the canister when estimating a total concentration of hemoglobin (e.g., free hemoglobin, intracellular hemoglobin) in the fluid contained therein.

In Block S120, selecting the second region of the image of the canister is preferably performed automatically at a module of the computing system. As such, in one variation, once an image of the canister is captured, (e.g., as described in U.S. patent application Ser. No. 13/738,919), Block S120 can comprise implementing machine vision techniques to identify the second region in the image, and/or one or more positional features associated with the second region in the image. For instance, in relation to a feature of an insert retained within the canister, as described further below, a position of the first region of the image, corresponding to a first feature of the insert, can be used to derive a position of the second region of the image, corresponding to a second feature of the insert, wherein the second feature of the insert provides the color gradient associated with fluid within the canister, and wherein the second feature has a known configuration relative to the first feature of the insert. Similar to Block S110, Block S120 can comprise implementing one or more of: object localization, segmentation (e.g., edge detection, background subtraction, grab-cut-based algorithms, etc.), gauging, clustering, pattern recognition, template matching, feature extraction, descriptor extraction (e.g., extraction of texton maps, color histograms, HOG, SIFT, etc.), feature dimensionality reduction (e.g., PCA, K-Means, linear discriminant analysis, etc.), feature selection, thresholding, positioning, color analysis, parametric regression, non-parametric regression, unsupervised or semi-supervised parametric or non-parametric regression, and any other type of machine learning or machine vision to identify the second region, and/or positional features that can be used to locate the second region of the image. However, Block S120 can alternatively include manually selecting the second region of the image, for instance, based upon a user input at an input module (e.g., touch pad, touch screen, mouse, etc.) in communication with the computing system. As such, a user input that selects the second region and/or indicates a boundary of the second region can alternatively be used in Block S120 to select the second region of the image exhibiting a color gradient.

In relation to the second region of the image exhibiting a color gradient, the second region of the image can be associated with a penetration depth of light through fluid within the canister and an absorption coefficient of light associated with fluid within the canister, wherein fluid at a shorter depth within the canister exhibits lighter color, and wherein fluid at a longer depth within the canister exhibits darker color. As noted in Section 2.1 below, the color gradient can be associated with incident light upon a surface of fluid within the canister (or originating from a feature of an insert within the canister). As such, Block S120 can include one or more of: providing incident light at a surface of fluid within the canister; retaining an insert within the canister with a feature of the insert in a configuration that transmits light through fluid within the canister; and performing any other suitable action that contributes to selection of the second region within the image of the canister.

However, the second region of the image can additionally or alternatively be associated with a second feature of an insert retained within or otherwise coupled to the canister, as described in Section 2.2 below. Block S120 can thus include one or more of: retaining an insert within the canister with a second feature of the insert in a set configuration, such that the insert provides a region of fluid, with a gradient in thickness, situated between a wall of the canister and the second feature; coupling an insert to the canister with a second feature of the insert in a configuration that contributes to the color gradient across the second region of the canister; generating image data of the canister and the second region of the canister, upon imaging the canister with an image acquisition device; and performing any other suitable action that contributes to selection of the second region within the image of the canister.

Additionally or alternatively, similar to Block S120, the second region of the image can correspond to an antiglare feature of an element applied or otherwise coupled to the canister, as described in U.S. application Ser. No. 14/687, 842, wherein an antiglare layer of a color grid element extends beyond the color grid element over a portion of the canister, in order to mitigate glare effects within image data of the canister. As such, variations of Block S120 can include retaining an insert within the canister with the second feature in a set configuration, and providing alignment between an antiglare region of an element applied to the canister and the second feature in the set configuration, thereby defining the first region of the canister. In a specific example, the antiglare layer of the color grid element extends over a portion of the canister and is in alignment with a feature of an insert, within the canister, that provides a layer of fluid, with a gradient in thickness, between the wall of the canister and the insert (in contributing to the color gradient across the second region); however, the second region of the image can be produced and/or detected in any other suitable manner.

2.1 Co-Axial Color Gradient

Figure 2:
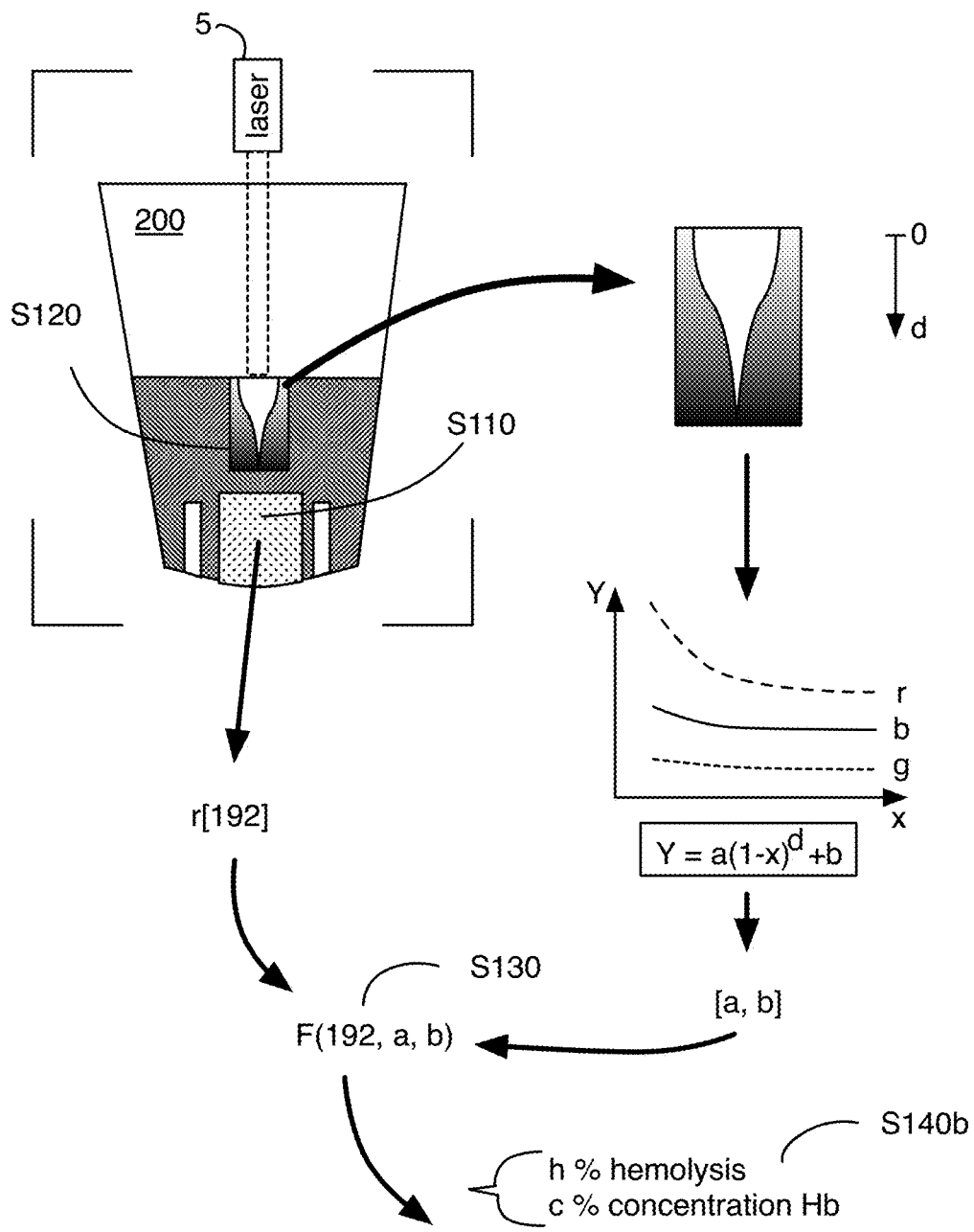
FIG. 2 is a flowchart representation of one variation of the method.

In a first variation, Block S120 includes selecting a color gradient initiated at or near the surface of the fluid in the canister and moving downward toward the base of the canister, as shown in FIG. 2. Generally, in this first variation, light incident on the surface of the fluid penetrates the surface of the fluid and is absorbed by the fluid as a function of both depth and an absorption coefficient of the fluid, wherein the absorption coefficient of the fluid is affected by both a concentration of a substance in the fluid and a type or size of the substance (e.g., either a whole red blood cell or free hemoglobin and ruptured cell matter). Thus, though a fluid in a canister may be of substantially uniform concentration with substantially uniform distribution of particulate, the fluid may appear visually light at the surface of the fluid and darker at a deeper portion of the fluid, with a smooth color gradient between the surface of the fluid and the deeper portion of the fluid. Block S120 can thus select all or a portion of this color gradient.

In one implementation, Block S120 includes identifying a meniscus at the surface of the fluid in the canister (such as described in U.S. application Ser. No. 13/738,919) and selects an upper edge of a bounding area of the second region at a particular distance (e.g., 2 mm or 20 pixels in the image) inferior to the identified meniscus. Block S120 can then set a lower edge of the bounding area at a fixed distance (e.g., 100 mm or 1000 pixels). Alternatively, Block S120 can include detecting a region (e.g., a pixel or a set of pixels) of the image below the superior edge of a bounding area at which the color of the fluid darkens by a threshold amount relative to a color of the fluid proximal the superior edge of the bounding area and set the lower edge of the bounding area at this area. Block S120 can thus include selecting a variable bounding area dependent upon fluid diluteness (or any other suitable factor that affects the color gradient), wherein a relatively 'tall' bounded area exhibiting a color gradient is selected for a canister containing a very dilute fluid, and wherein a relatively 'short' bounded area exhibiting a color gradient is selected for a canister containing a high concentration of red blood cells. Block S120 can include then connect the superior and inferior edges with vertical edges of a suitable spacing—such as with a spacing of one pixel or ten pixels—to close the bounded area, and then lock or shift the bounded area over the image of the canister, such as centered horizontally over the canister. Alternatively, Block S120 can align the bounded area with a region of the canister exhibiting low glare. For example, Block S120 can analyze the image to identify an anti-glare surface, coating, or transparent laminate applied to the canister—as described in U.S. patent application Ser. No. 13/738,919—and then align the bounded area with this anti-glare surface.

Similarly, Block S120 can identify a base region of the canister and set the lower edge of the bounded area on or near the base region of the canister and then implement methods as described above to set the upper edge of the bounded area above the lower edge. However, in this first variation, Block S120 can select the second region of the image containing the color gradient in any other suitable way, for instance, by selecting a bounding region for the color gradient at an intermediate portion of the fluid within the canister (i.e., away from the surface of the fluid and away from the base region of the canister).

In this first variation, the method 100 can also include implementing a light source coupled to, integrated into (e.g., integrated into an insert), or otherwise configured to illuminate fluid within the canister. In this first variation, the light source 5 can be coupled to or configured to illuminate a surface of fluid within the canister and/or a surface of the canister, and in variations wherein the light source 5 is coupled to the canister, the light source can be coupled to any suitable portion of the canister (e.g., a wall of the canister, a lid of the canister, an insert coupled to the canister, etc.). In one example, the canister mounts into a lid supported by a surgical suction machine, wherein the lid includes a laser module configured to direct coherent light into fluid within the canister. In an example, the laser module can include an output optic directed in a superior-to-inferior direction, thereby transmitting light toward the center of the base of the canister. Thus, in this example, before capturing an image of the canister, Block S120 of the method 100 can include triggering a laser diode coupled to the laser output optic (e.g., via a fiber optic cable) to output an energy beam, thereby illuminating fluid contained in the canister. In a similar example, a florescent or incandescent bulb is arranged over the canister, such as integrated into the lid of the canister or clipped to a rim of the canister (or otherwise configured relative to any other suitable surface of the canister), and the bulb remains 'ON' on during a surgery or is trigged 'ON' (just) before an image of the canister is captured, thereby illuminating the fluid from above (or from any other suitable perspective). Alternatively, the canister can include a light source 5 arranged under a base of the canister and directed upward toward the top of the canister, such as along a longitudinal axis of the canister. For example, the light source 5, a power source, and a (wired or wireless) controller can be integrated into the base of the canister, and the method 100 executing on a computing device proximal the canister can include transmitting a signal to the controller (e.g., of I2C wired communication protocol or over Bluetooth wireless communication protocol) to trigger the power source to supply power the light source 5. In another example, an aftermarket fluid illuminator is coupled to the canister, wherein the aftermarket fluid illuminator includes a housing that clips onto or otherwise attaches to an exterior surface of the canister or that rests inside the canister, and wherein a light emitter within the aftermarket fluid illuminator is directed toward the internal volume of the canister and is manually turned "ON" before or during surgery, or is automatically controlled as described above, such as by wirelessly pairing (e.g., over Bluetooth) the aftermarket fluid illuminator with a computing device on which Blocks of the method execute. However, the method can interface with any other light emitter integrated into the canister, installed on or in the canister (e.g., in relation to an insert 300, as described below), attached to the canister, or integrated or installed onto a surgical suction machine supporting the canister during a surgery or other medical event.

In variations involving a light source 5, the light source can be configured to emit wavelengths of light spanning or otherwise associated with one or more absorbance peaks in an absorbance spectrum for one or more target components of fluid within the canister. For instance, the light source can be configured to provide a broad range of wavelengths of light, narrower ranges of wavelengths of light, or alternatively a discrete wavelengths of light corresponding to one or more absorbance peaks of a target component of the fluid in the canister. For instance, in relation to hemoglobin, the light source 5 can be configured to provide wavelengths of light from ~400-700 nm (e.g., corresponding to an absorbance peak from 500-600 nm, corresponding to an absorbance peak at 525 nm, corresponding to an absorbance peak at 575 nm), and wavelengths of light from 800-950 nm (e.g., corresponding to an absorbance peak from 850-900 nm, corresponding to an absorbance peak at 870 nm). Additionally or alternatively, in relation to hemoglobin, the light source 5 can be configured to provide wavelengths of light associated with absorbance peaks/spectra of one or more forms of hemoglobin (e.g., oxygenated hemoglobin, sulfhemoglobin, methemoglobin, etc.), in order to enable differentiation in colors of fluid and/or color gradients of fluid associated with different forms of hemoglobin. However, the light source can alternatively be configured to emit wavelengths of light corresponding to absorbance spectra of any other suitable component of fluid within the fluid canister.

Thus, as in the foregoing examples, Block S120 can also include identifying a portion of the image corresponding to a point or area on which light from an adjacent light source is initially incident on the fluid and select the second region of the image—exhibiting a color gradient—that extends from this point or area. For example, Block S120 can include initially identifying the canister in the image, identifying a portion of the image corresponding to an anti-glare surface on the canister, testing individual pixels or clusters of pixels within this portion of the image for a greatest brightness, and identifying a particular individual pixel or cluster of pixels of greatest brightness in this portion of the image as the initial point of incidence of light on the fluid. Block S120 can then include selecting the second region—including the color gradient—that extends from this particular pixel or pixel cluster, such as by selecting a portion of the image extending downward from the particular pixel or pixel cluster associated with the light source that is known to be arranged above the canister, or by selecting a portion of the image extending upward from the particular pixel or pixel cluster associated with a light source 5 that is known to be arranged under a base of the canister.

However, Block S120 can function in any other way to select the second region of the image that includes a color gradient corresponding to absorption of light from an external light source by fluid in the canister.

In this first variation, Block S110 can then include selecting the first region of the image distinct from the second region and exhibiting a substantially uniform color (e.g., in terms of hue, saturation/chroma, and brightness/value). In particular, as described in U.S. patent application Ser. No. 13/738,919, Block S120 can include selecting a region of the image coincident with an anti-glare surface on the canister and substantially removed from the second region. For example, upon selection of a second region extending from a top surface of the fluid downward toward a base of the canister, Block S120 can quantify absorption of light downward from the surface of the fluid as a percentage of light absorption (or intensity of incident light), and Block S110 can bound a top edge of the first region at a horizontal line of pixels offset (e.g., by 10 pixels) downward from a particular pixel vertically below a point of initial light incidence on the surface of the fluid and associated with a point of 99% absorption of light from a (local or ambient) light source (or 1% intensity of the initial intensity of the incident light). Alternatively, Block S110 can analyze the image to identify a portion of the image corresponding to fluid within the canister and then identify a largest area of contiguous pixels (or pixel clusters) with less than a threshold difference in value (e.g., less than a 2% change in color value in the red spectrum, less than a 4% change in color value in the green spectrum, and less than a 5% change in color value in the blue spectrum). Yet alternatively, Block S110 can identify a region of the image of a target dimension (e.g., 50 pixels by 50 pixels) and/or target size (e.g., 200 contiguous pixels) exhibiting less than a threshold change in color, shade, or tint. However, Block S110 can function in any other way to select the first region of the image exhibiting a substantially uniform color in any other suitable way. Furthermore, in relation to the first variation, involving a co-axial color gradient, Blocks S110 and S120 can be performed in any other suitable order and in any other suitable alternative manner.

2.2 Canister Insert and Cross-Axial Color Gradient

In a second variation, Block S110 includes selecting the first region of the image that corresponds to a layer of fluid between a wall of the canister and a first feature within the canister, along a line of sight between the canister and a camera or (other optical sensor of an image acquisition device) that captures the image. Optionally, Block S120 can include selecting the second region of the image that corresponds to a region of fluid, having a gradient in thickness, between a wall of the canister and a second feature within the canister, along the line of sight, as shown in FIGS. 1A and 1B. In particular, the first feature in this second variation is offset from the wall of the canister at a substantially uniform distance such that a "layer" of fluid between the wall of the canister and the first feature is of substantially uniform thickness across the first feature, and the second feature tapers away from the wall of the canister such that the total "thickness" of "layers" of fluid between the wall of the canister and the second feature increases with a known profile (e.g., linear profile, non-linear profile, stepwise function profile, etc.), such as relative to an edge of the second feature nearest the image acquisition module.

Figure 3A:
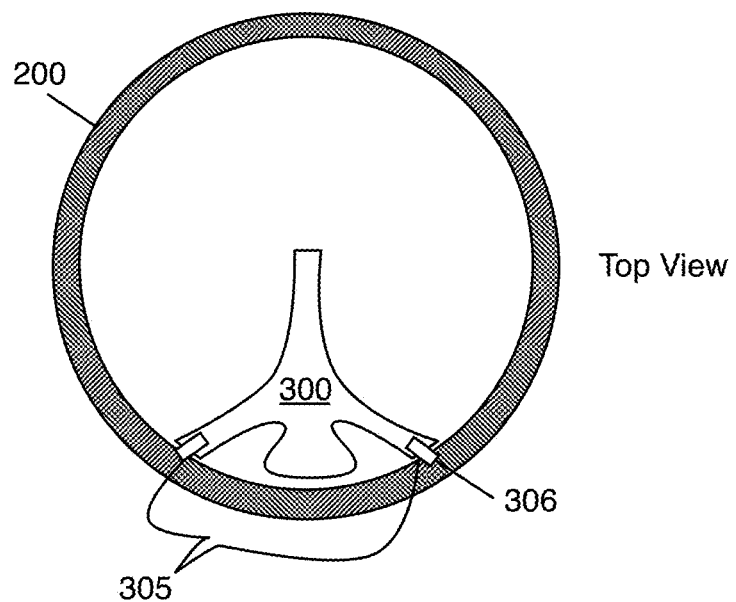
FIGS. 3A and 3B depict schematics of variations of an insert in an embodiment of the method and system for estimating a quantity of a blood component in a canister.

The first feature 310 and/or the second feature 320 can be coupled to an insert 300 configured to be retained within the canister 200 in a first operation mode, with the first feature 310 and/or the second feature 320 in a set configuration relative to the canister. Furthermore, as shown in FIG. 3A, retention of the insert 300 within the canister 200 can be permanent or reversible, for instance, by way of a locking feature (e.g., of the canister 200 and/or of the insert 300) that irreversibly or reversibly locks the insert 300 in a set configuration within the canister 300. Variations of the locking feature 305 can include one or more of: a protrusion 306 (e.g., rail, etc.) on at least one of the canister 200 and the insert 300, that mates with a recess (e.g., slot, etc.) on the other one of the insert 300 and the canister 200; magnetic features (e.g., complementary magnets coupled to the insert 300 and the canister); a mechanical press fit mechanism between a portion of the canister 200 and a portion of the insert; a mechanical snap fit between a portion of the canister 200 and a portion of the insert; and any other suitable locking feature 305. However, in some variations, the first feature 310 and/or the second feature may alternatively not be a feature of an insert 300, and can be of unitary construction with an internal portion of the canister 200. Furthermore, some variations of the canister 200 and/or the insert 300 can omit a second feature 320, and only include a first feature 310 configured to define a region of substantially uniform color within an image of the canister.

The insert 300 is preferably composed of a material that is white, opaque, and impermeable to fluid within the canister, in order to provide the region of uniform color and/or the color gradient region. However, the insert 300 can alternatively be composed of a material that is one or more of: non-white, non-opaque (e.g., having some degree of transparency), and not impermeable to fluid within the canister. For instance, in some variations, the insert 300 can have a color (e.g., non-white color) or pattern (e.g., grid, matrix barcode, QR code) that is observable through the region of fluid between the insert 300 and the canister 200, in supporting subsequent blocks of the method 100. The pattern can be coupled to a portion of the insert 300 in direct contact with an inner surface of the canister, or can alternatively be coupled to a portion of the insert 300 not in direct contact with an inner surface of the canister. For instance, in relation to the color grid of Ser. No. 14/687,842, a color grid or matrix barcode coupled to the insert and observable through the region of fluid between the insert 300 and the canister 200 can be used to determine fluid parameters (e.g., fluid component concentrations) associated with fluid within the canister 200. For instance, in one application, a color grid including a set of regions of color, each region associated with a blood component concentration, can be applied to the insert. In this application, an inability of a detection system to identify one or more color regions of the color grid, through fluid within the canister, can be used to determine a blood component concentration associated with fluid within the canister. In more detail, a detection system can identify a color region on the insert 200, that is unobservable through fluid within the canister, associate the color region with a blood component concentration, and determine an amount of the blood component within the canister 200 based upon a volume of fluid within the canister. In an alternative to this application, an analysis of a difference in color between each color region, observed through fluid within the canister, and a color of fluid within the canister, can be used to similarly estimate a blood component concentration for fluid within the canister. In still another alternative to this application, a color "grid" exhibiting a gradient in color (e.g., by including a pattern having successively blurrier edges between regions of the pattern) can be used to assess a level of hemolysis, in relation to a gradient in color within fluid of the canister.

Figure 3B:
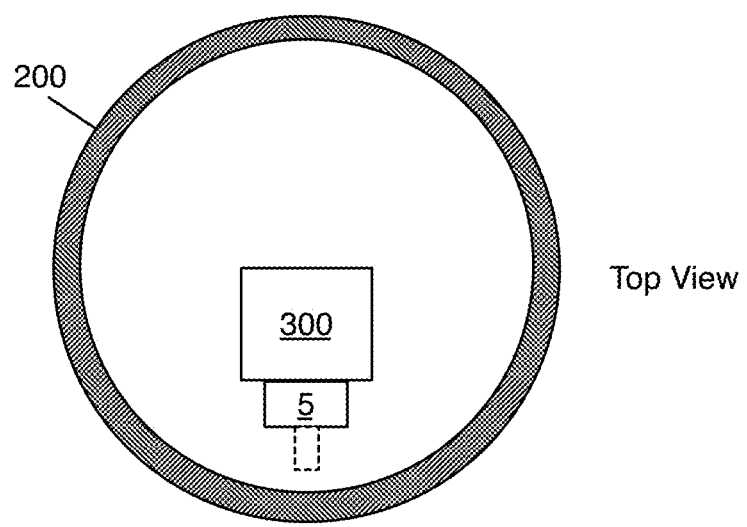

Furthermore, in relation to a light source 5 configured to transmit light through a portion of fluid within the canister 200, the light source 5 can be integrated within the insert 300 or otherwise coupled to the insert 300, as shown in FIG. 3B, in order to transmit light through fluid within the canister 200. As such, the insert 300 can be composed of, or include features composed of a material configured to transmit light from the light source 5 in a desired manner. In variations, the material can function as a light pipe (e.g., as in fiber optics), configured to direct light from the light source 5 along and/or to a surface of the insert 200 in contact with fluid within the canister 200. Alternatively, the material of the insert 300 can be configured to transmit light from the light source 5 in a diffuse manner through fluid within the canister 300. However, the light source 5 and/or the insert 300 be configured in any other suitable manner. Features of the insert 300 can, however, enhance implementation of the method 100 in any other suitable manner.

Figure 4:
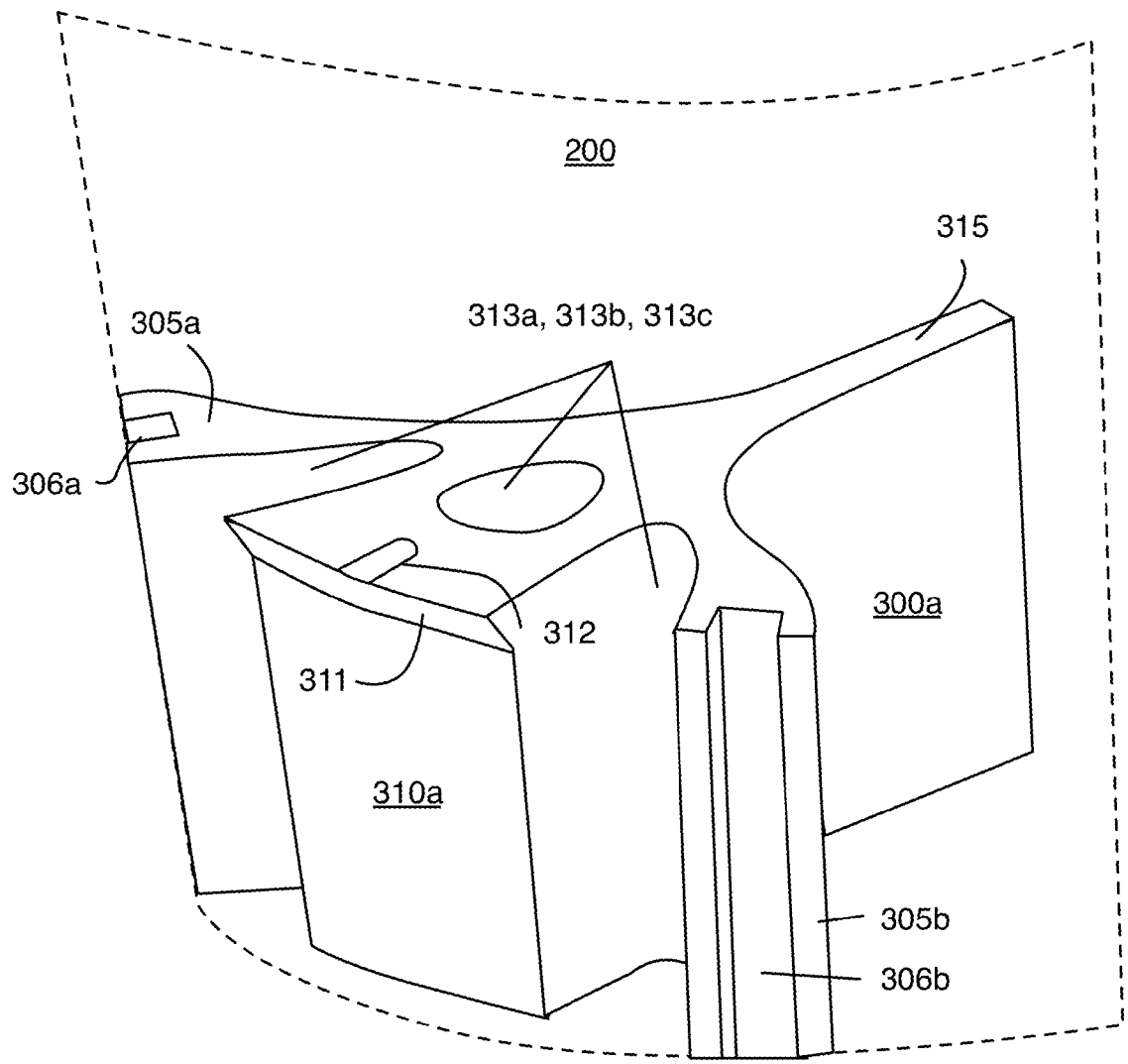
FIG. 4 depicts a first implementation of an insert in an embodiment of the method and system for estimating a quantity of a blood component in a canister.

In a first implementation of the variation of the canister 200 including an insert 300a, as shown in FIG. 4, the insert 300 includes a first alignment arm 305a and a second alignment arm 305b, each including a slot that complements an associated protrusion 306a, 306b configured at an internal surface of the canister 200, wherein the first and the second alignment arms 305a, 305b and the protrusions 306a, 306b function as a locking feature 305. In this first implementation, the first and the second alignment arms 305a, 305b surround (e.g., sandwich) a first feature 310a of the insert configured to provide the region of uniform color, wherein the first feature 310a has a surface displaced from an internal surface of the canister 200 by a constant distance. In the first implementation, the first alignment arm 305a and the second alignment arm 305b are radially displaced from each other in surrounding the first feature 310a, and the insert 300a has an axis of symmetry, such that the position of the first alignment arm 305a mirrors the position of the second alignment arm 305b about the first feature 310a.

In the first implementation, a superior edge of the first feature 310a includes a lip 311 configured to contact an adjacent internal portion of the canister 200, wherein the lip 311 includes an alignment flange 312 configured to facilitate alignment between the canister 200 and the insert 300a. The lip 311 further functions to block light rays that could otherwise penetrate the imaging region associated with the first feature 310a of the canister 200 and confound any measurements. As such, color features extracted from the imaging region are derived from backscattering or ambient light (which is accounted for, for instance, by a color grid as in U.S. application Ser. No. 14/687,842), and backlighting from the first feature 310a of the insert 300a. Variations of the first implementation of the insert 300a can, however, omit a lip 311, and image processing methods can account for any light rays that penetrate the imaging region associated with the first feature, in relation to the insert 300a without a lip 311. The insert 300 of the first implementation further includes a set of gaps 313a, 313b, 313c configured to allow fluid within the canister 200 to flow into the first feature 310a. In particular a first gap 313a is configured laterally between the first alignment arm 305a and the first feature 310a, and a second gap 313b is configured laterally between the second alignment arm 305b and the insert; however, in alternative variations of the first implementation, the set of gaps 313a, 313b, 313c can be configured in any other suitable manner. Finally, the insert 300a of the first implementation includes a grip handle 315 configured at a posterior portion of the insert 300a that enables the user or another entity to position the insert 300 within the canister 200, and apply a "downward" force to push the insert toward the base of the canister 200.

Figure 5:
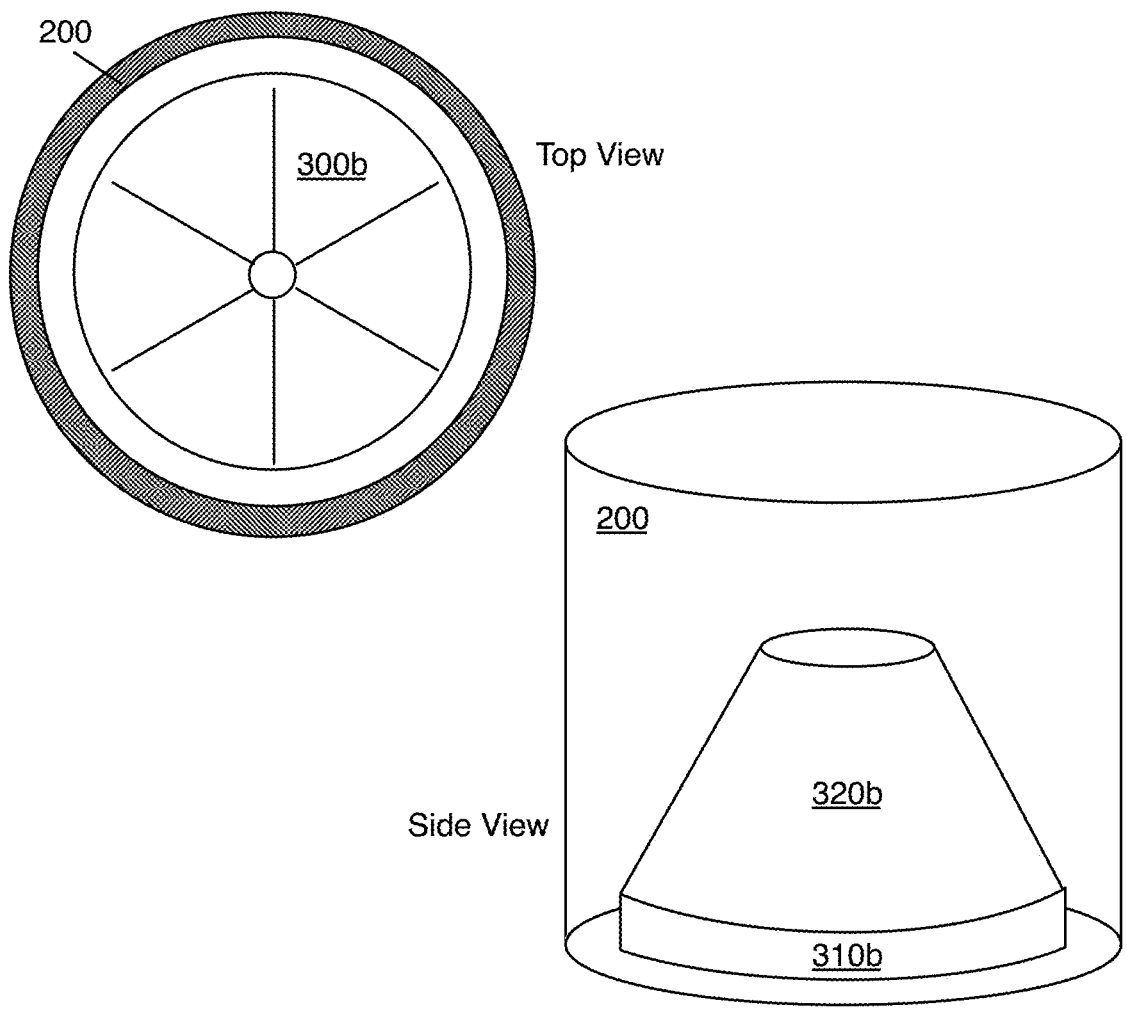
FIG. 5 depicts a second implementation of an insert in an embodiment of the method and system for estimating a quantity of a blood component in a canister.

In a second implementation of the variation of the canister 200 including an insert, as shown in FIG. 5, an insert 300b defining the first feature 310b and the second feature 320b is configured to be installed in the canister 200 prior to use in receiving bloodied fluid from a patient. In the second implementation, the insert 300b defines a frustoconical structure 320b with a cylindrical base 310b that snaps into the base of the canister 200, as shown in FIG. 5, wherein the insert 300b is manufactured from a highly-reflective (i.e., glossy) white polymer material and/or is coated with a white glossy material. In this example, the outer surface of cylindrical base 310b is displaced from an interior surface of the canister 200 when the insert 300b is installed therein, such as by ~6 mm (e.g., an average of 6 mm), such that a layer of fluid between the interior surface of the canister 200 and the cylindrical base 310b yields a substantially uniform color in the corresponding region of the image of canister; Block S110 can thus identify and select this region of the image. Furthermore, in this example, the frustoconical structure 320b can taper toward a center portion of the canister 200 (e.g., at a slope of 0.5 or at an angle of 30°) in an inferior to superior direction, thereby yielding a color gradient in a portion of the image corresponding to a region of fluid between the interior surface of the canister 200 and the frustoconical structure 320b, as less ambient light reaches and is reflected back from the frustoconical structure 320b, and as the thickenss of the fluid region between the interior wall of the canister and the frustoconical structure increases; Block S120 can thus identify and select this region of the image. Blocks S110 and S120 can also cooperate to identify an edge between the frustoconical structure and the cylindrical base and then distinguish between the frustoconical structure and the cylindrical base based upon a color gradient and color uniformity on each side of the edge.

Figure 6:
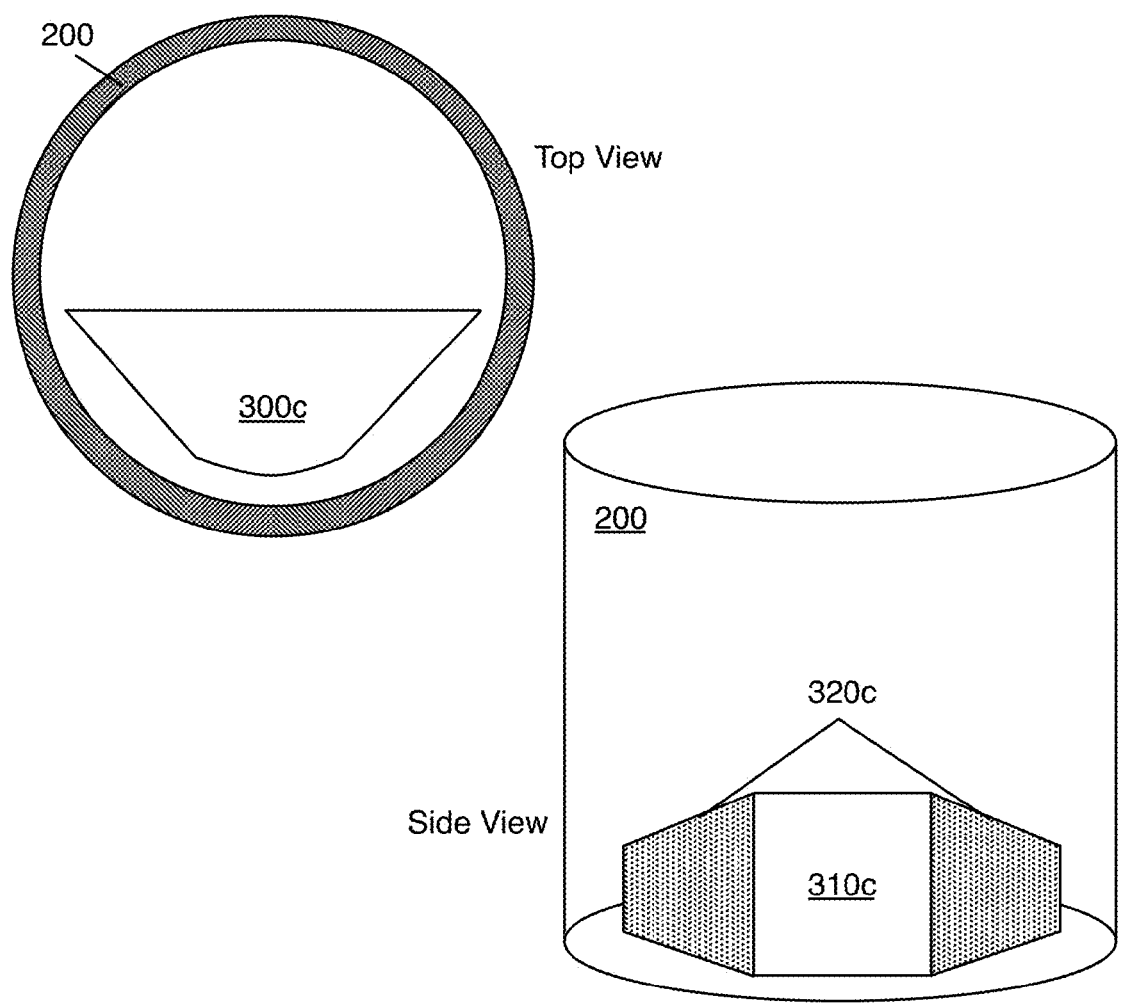
FIG. 6 depicts a third implementation of an insert in an embodiment of the method and system for estimating a quantity of a blood component in a canister.

In a third implementation of the variation of the canister 200 including an insert, when the insert 300c is installed in a canister 200, the first feature 310c defines a first vertical surface (e.g., planar surface, curved surface) that faces (e.g., squarely faces) and is offset from the interior wall of the canister, such as by ~6 mm, and the second feature 320c defines a second vertical surface tapering away from (e.g., with a linear profile, with a non-linear profile) an interior surface of the canister 200, the first and second features 310c cooperating to define a sharp vertical edge, as shown in FIG. 6. As in the previous example, the substantially uniform thickness of a layer of fluid between the interior surface of the canister 200 and the first feature 310c can yield a substantially uniform color in the corresponding region of the image, and the increasing thickness of the region of fluid between the interior surface of the canister 200 and the second feature 320c along the length of the second feature 320c can yield a color gradient across the corresponding region of the image.

Figure 7:
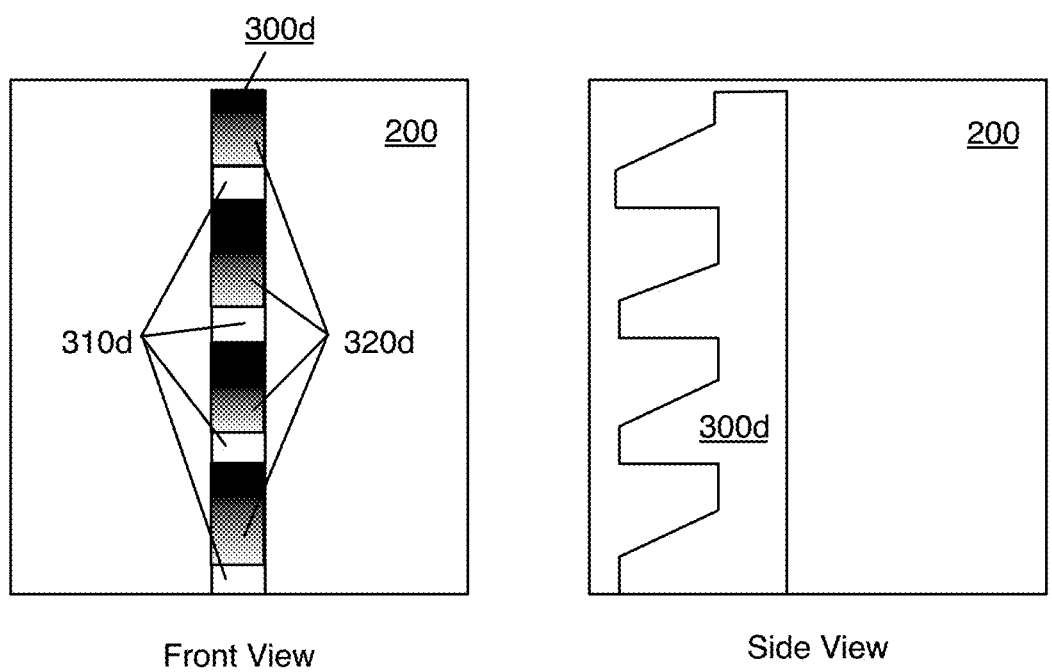
FIG. 7 depicts a fourth implementation of an insert in an embodiment of the method and system for estimating a quantity of a blood component in a canister.

In a fourth implementation of the variation of the canister 200 including an insert, the insert 300d can include a elongated member defining a sawtooth cross-section with a (substantially) planar at the tip of each tooth, as shown in FIG. 7, wherein the each planar tip defines a first feature 310d, and wherein the taper of each sawtooth defines a second feature 320d. Because the volume of fluid in the canister 200 may change over time (i.e., during a surgery) and because particulate (e.g., lipids) in the fluid may float or sink in the fluid, this geometry of the insert 300d can provide multiple first and second features 310d, 320d that yield multiple corresponding regions of substantially uniform color and multiple corresponding regions exhibiting color gradients such that, despite a volume of fluid in the canister and/or an amount of undissolved solids in the canister, Blocks S110 and S120 can identify and select at least one suitable first region and one suitable second region, respectively, in the image of the canister.

Figure 8:
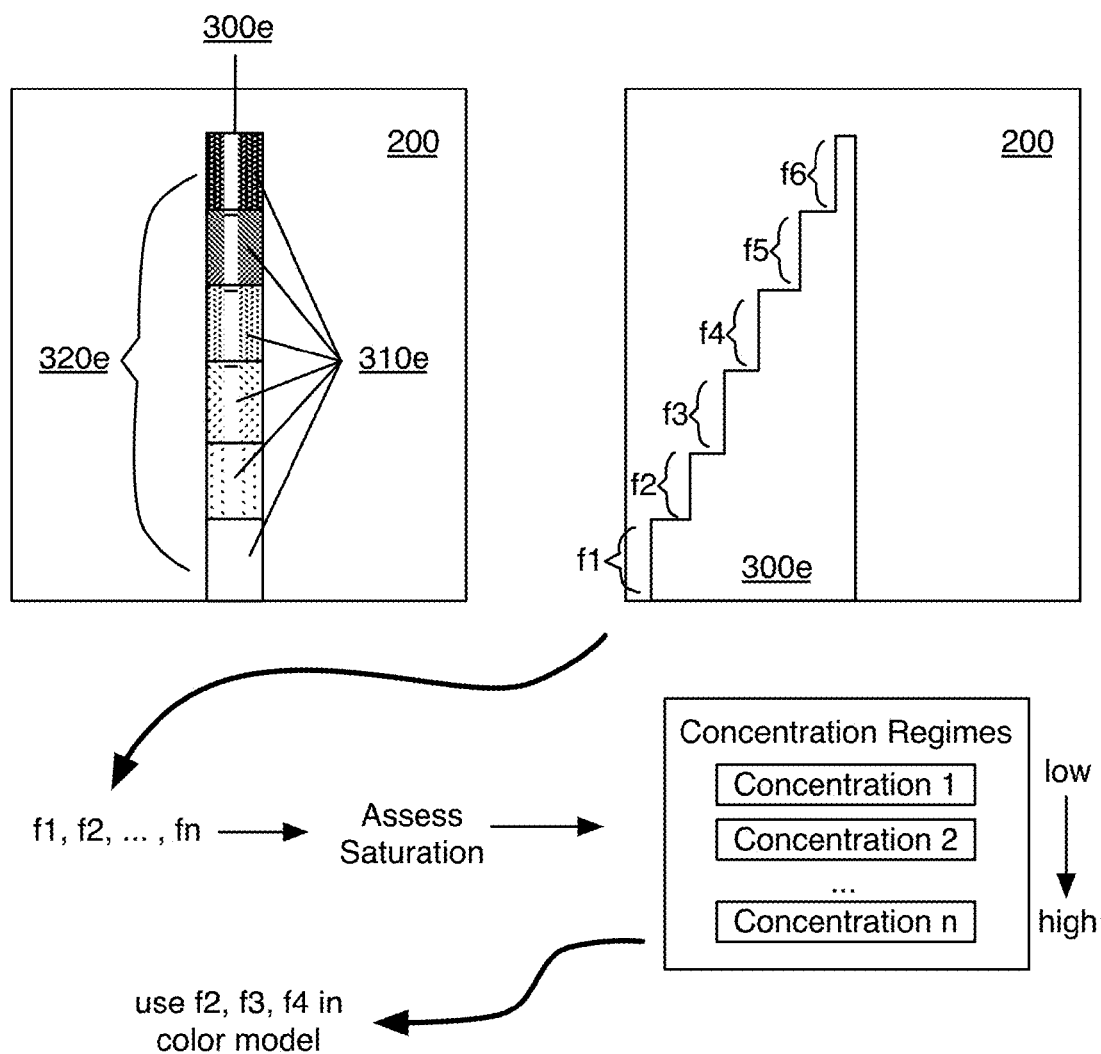
FIG. 8 depicts a fifth implementation of an insert in an embodiment of the method and system for estimating a quantity of a blood component in a canister.
Figure 9:
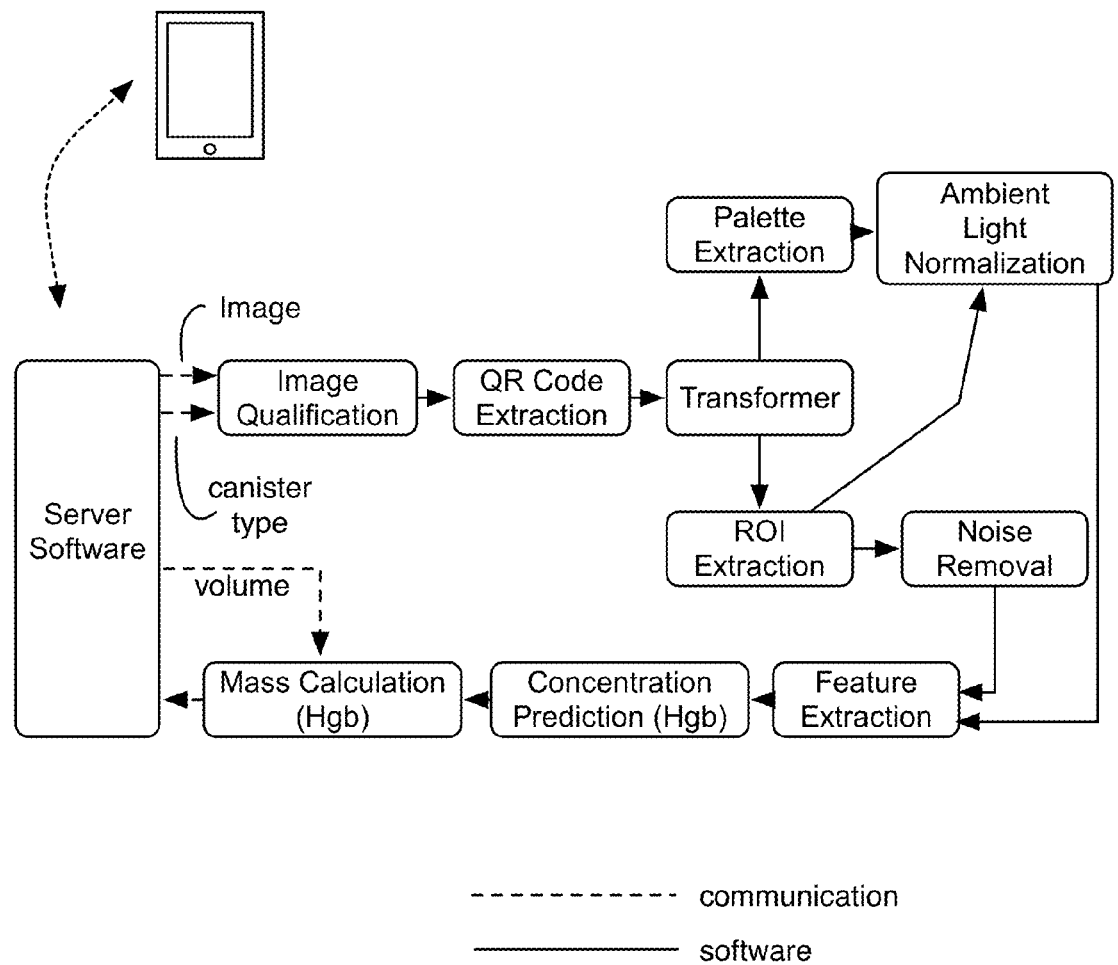
FIGS. 9-12 depict schematics of specific systems configured to implement an embodiment of the method for estimating a quantity of a blood component in a canister.
Figure 10:
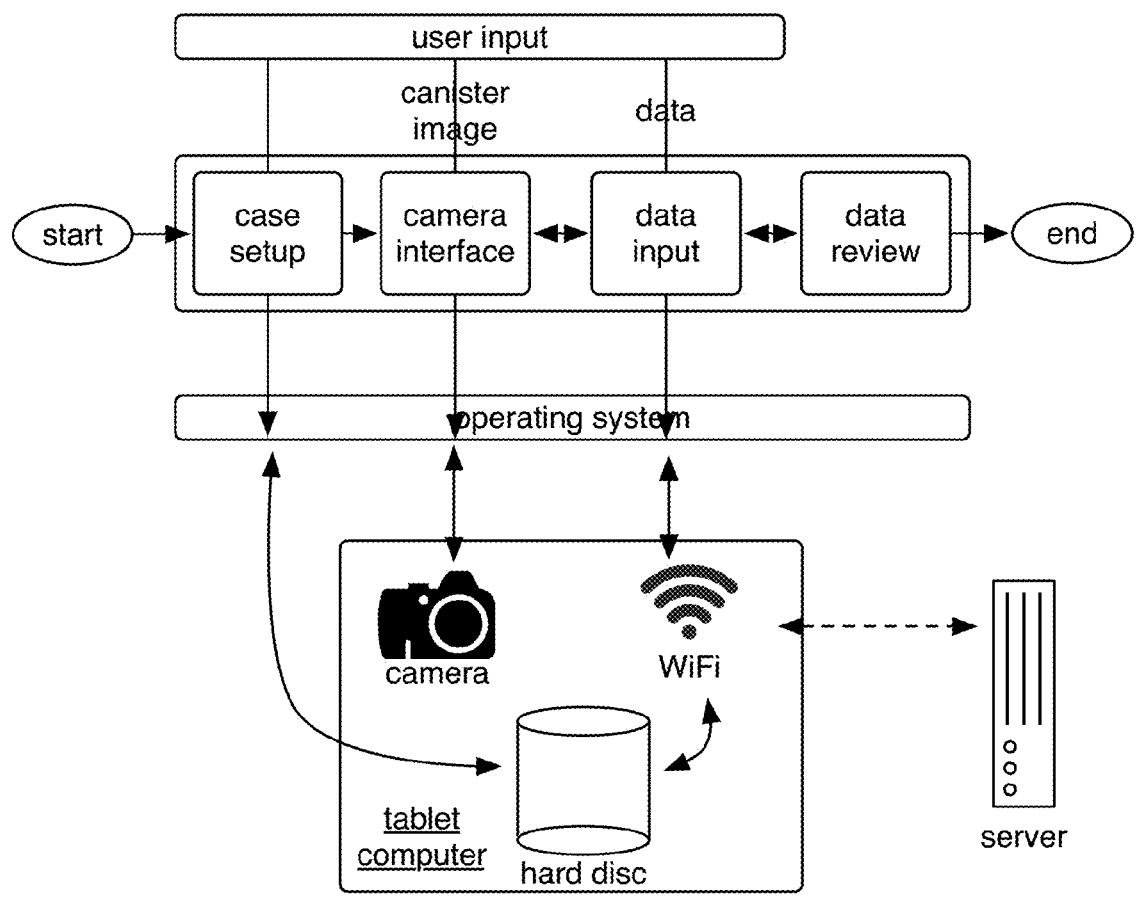
Figure 11:
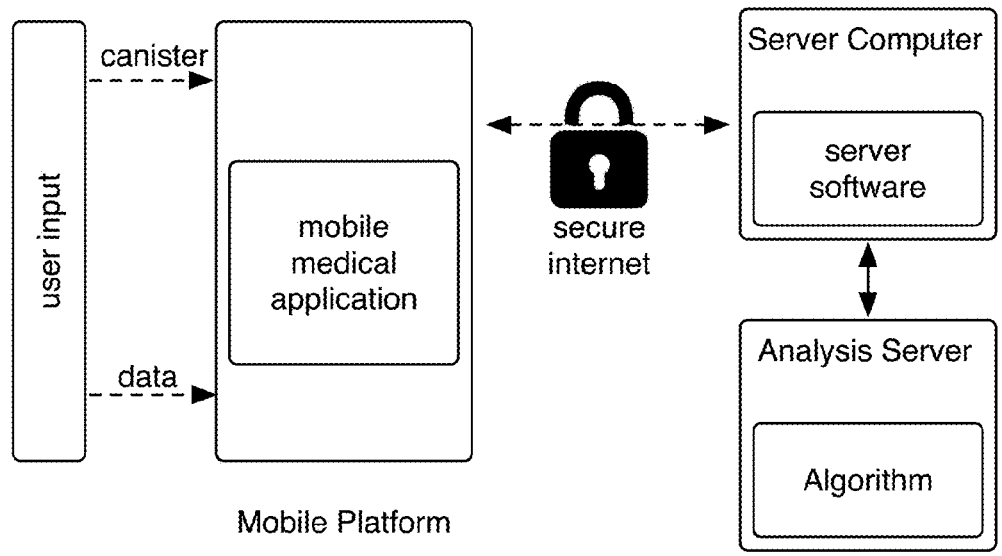
Figure 12:
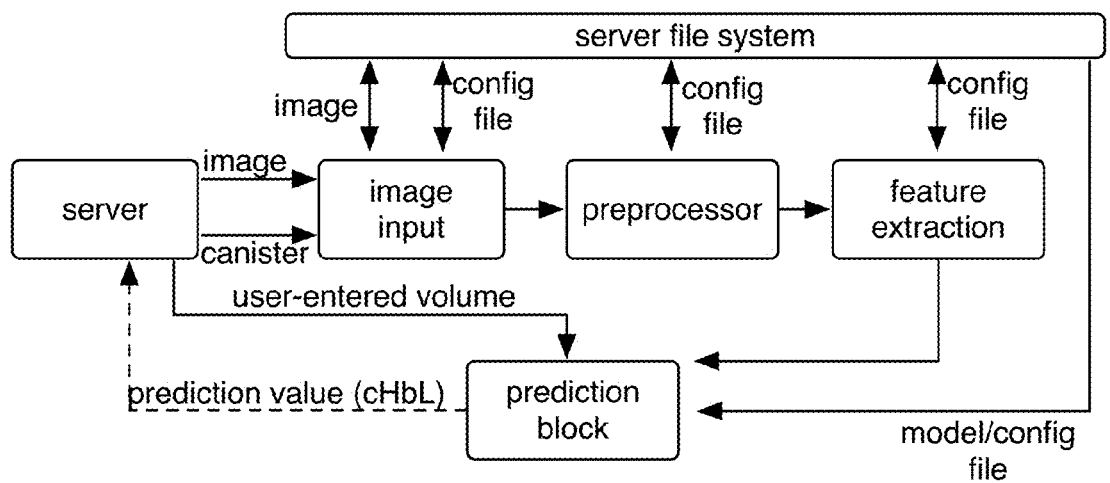

In a fifth implementation of the variation of the canister 200 including an insert, the insert 300e can include stepped configuration defined by a set of first features 310e, as shown in FIG. 8, wherein each of the set of first features 310e is offset from an internal surface of the canister 200 by a certain distance (e.g., in order to provide a region of uniform color, with a region of fluid between the surface of the canister and each of the first features of the insert). In the fifth implementation, each of the set of first features 310e is further displaced from an adjacent first feature by a distance (e.g., with uniform spacing, with non-uniform spacing), such that collectively, the set of first features 310e defines a second feature 320e that provides a color gradient along a dimension of the insert 300e. In the fifth implementation, the set of first features 310e can be arranged such that the first features 310e traverse deeper into the canister in an inferior to superior direction, arranged such that the first features 310e traverse deeper into the canister in a superior to inferior direction, or alternatively traverse deeper or shallower in relation to a surface of the canister in any other suitable configuration. Thus, Blocks S110 and S120 can identify and select at least one suitable first region and one suitable second region, respectively, in the image of the canister.

In relation to the fifth implementation, Blocks S110 and/or S120 can include selecting and analyzing regions corresponding to each of the set of first features 310e, in order to extract a parameter (e.g., color parameter) from each region, as shown in FIG. 8. Each parameter (e.g., f1, f2, f3, . . . , fn) can then be processed (e.g., with a color model, as described above), in order to determine a concentration of a blood component associated with fluid within the canister. Additionally or alternatively, each parameter (e.g., f1, f2, f3, . . . , fn) can be used to classify fluid within the canister into one of a set of regimes (e.g., a high concentration regime, a medium concentration regime, a low concentration regime, one of a set of hemolysis regimes, etc.), wherein in each of the set of regimes, a subset of the set of parameters (e.g., only f2-f4) are used to determine one or more characteristics of the fluid within the canister 200 using a discrete model. In relation to the fifth implementation and any other implementation of the insert 300, other regions of an image associated with the canister 200 that are not directly associated with presence of an insert 300 (e.g., bulk fluid regions within the canister) can be used to extract features. As such, in one example, a bulk solution color feature can be compared to a color feature associated with a portion of an insert 300 (e.g., a ratio can be determined, a difference can be determined, etc.), wherein one or more of the bulk solution color feature and the color feature associated with the insert can be used to determine an amount of a fluid component within the canister. Additionally or alternatively, the comparison and/or color features can be used to classify fluid within the canister into one of a set of regimes, as described above, in order to select one of a set of color models to characterize fluid within the canister. Processing parameters derived from the insert 300e of the fifth implementation and variations thereof can, however, be performed in any other suitable manner.

Furthermore, in alternatives to any of these implementations, the insert can be of any other suitable material, surface finish, and/or color and can define a first feature and a second feature of any other suitable form. Even further, Blocks S110 and S120 can also function in any other way to identify a first region of the image of substantially uniform color and a second region exhibiting a color gradient in any other suitable way. Blocks S110 and S120 can also select multiple instances of first and second regions, respectively. For example, Block S120 can select a "second region" corresponding to a color gradient arising from ambient light incident on a surface of the fluid and another "second region" corresponding to a tapered feature of an insert 300 installed within the canister 200. As such, variations of the above implementations can be combined in any suitable manner.

3. Blood Component Concentration and Amount

Block S140 recites: determining a concentration of the blood component in the canister based upon a color parameter representative of the first region of the image. As described in U.S. application Ser. Nos. 13/544,646, 13/894, 054, 13/738,919, 14/072,625, and 14/687,842, Block S140 can include implementing one or more of a parametric model and a template matching algorithm to determine the concentration of the blood component associated with fluid within the canister. In one variation, Block S140 can implement a parametric model to determine the concentration of the blood component (e.g., hemoglobin) within the sample, wherein the parametric model implements a support vector machine (SVM) algorithm with a radial basis function (RBF) kernel that generates a hemoglobin concentration derived from red value, green value, and blue value color intensities representative of the first region of the image, and multiplies the hemoglobin concentration by the volume of fluid within the canister can to determine the estimated hemoglobin mass. Additionally or alternatively, any other suitable parametric model (e.g., linear regression model, power curve driven regression model, other regression model, etc.) or a non-parametric model can be implemented by the processing system to determine an amount of any other suitable blood component within the canister (or other fluid receiver).

In some variations, Block S140 can further include determining a hemolysis status of fluid within the canister, which functions to enhance outputs of the method 100 with information pertaining to quality of the fluid contained within the canister (e.g., in relation to usability for transfusion, etc.). Block S140 can include receiving information indicative of a concentration of free hemoglobin and a concentration of intracellular hemoglobin present in fluid within the canister, thereby enabling determination of a distribution of free hemoglobin vs. intracellular hemoglobin within the canister. In one variation, Block S140 can include receiving information pertaining to the hemolysis status from an entity interacting with the system, wherein information pertaining to free hemoglobin vs. intracellular hemoglobin can be manually input (e.g., with keypad strokes, by speech, etc.) into an input module of a computing device of the system. In an example of this variation, a holistic blood loss management application executing at a mobile computing device (e.g., tablet computer, smartphone device, etc.) can include a user interface configured to receive an input indicative of the hemolysis status within the canister, wherein the input is provided by a physician, nurse, assistant, or technician present within an operating room environment. Then, as described in Section 6 below, a free hemoglobin concentration and/or an intracellular hemoglobin concentration can be processed with volume information in Blocks S150 and S151, in order to determine an amount hemoglobin present within fluid in the canister, as well as an amount of free vs. intracellular hemoglobin present within fluid in the canister.

Additionally or alternatively, a second region of the image, corresponding to a color gradient (e.g., as in Block S120), can be used to estimate a hemolysis status of fluid within the canister, as described in Blocks S130 and S140$b$ below. Then, in a manner similar to that described in Block S140 above, outputs of Block S140$b$ concentration can be processed with volume information in Blocks S150 and S151, in order to determine an amount hemoglobin present within fluid in the canister, as well as an amount of free vs. intracellular hemoglobin present within fluid in the canister.

4. Canister Content Model

As noted above, variations of the method 100 that include Block S120 can include Block S130, which recites: selecting a canister content model based on a characterization of the color gradient in the second region of the image. In one implementation, Block S130 selects a single line of pixels along the second region, decomposes the color of each pixel in the line into red, green, and blue components, plots a brightness in the red component space for each pixel, and calculates a line of best fit for the plotted values. For example, Block S130 can fit an exponential curve to a line of pixels in a co-axial color gradient as selected in the first variation described above, and Block S130 can fit a logarithmic curve to a line of pixels in a cross-axial color gradient as selected in the second variation described above.

In a similar implementation, Block S130 can group adjacent pixels within the second region of the image into clusters, average or otherwise synthesize color values within each cluster of pixels, decompose the color of each pixel cluster into the line into red, green, and blue components, plot a brightness (or color) in the red component space for each pixel cluster, and calculate a line of best fit for the plotted brightness values.

Block S130 can subsequently select one or more of: an algorithm, a parametric model, or a series of template images, based on one or more coefficients of the line of best fit thus calculated. For example, Block S130 can fit a line of the formula $Y=a(1-x)^d+b$ to the color gradient, compare the calculated coefficient 'a' to value ranges associated with various algorithms, models, template image sets, etc. In this example, a database can include models A, B, C, D, and E, wherein model A covers a hemolysis range of 0-20% and corresponds to 'a' coefficient values of a≤10, wherein model B covers a hemolysis range of 20-40% and corresponds to 'a' coefficient values of 10<a≤14, wherein model C covers a hemolysis range of 40-60% and corresponds to 'a' coefficient values of 14<a≤19, wherein model D covers a hemolysis range of 60-80% and corresponds to 'a' coefficient values of 19<a≤22, and wherein model E covers a hemolysis range of 80-100% and corresponds to 'a' coefficient values of 22<a. Thus, in this example, for a=21.7435, Block S130 can select Model D and estimate a hemolysis level in the canister at between 60% and 80%.

Alternatively, Block S130 can calculate an absorption coefficient of the fluid from the color gradient and pass this value directly to Block S140$b$ or select a canister content model corresponding to this absorption coefficient.

In one variation in which Blocks S110 and S120 select regions of the image corresponding to first and second features of an insert arranged in the canister, Block S130 can additionally or alternatively determine a sharpness parameter associated with a junction (i.e., an edge) between the first and second features, as described above, and process the sharpness parameter according one or more of: a particular algorithm, a parametric model, a series of template images, and any other suitable model or algorithm. For example, sharper edge definition in an image of a first canister may indicate that the first canister has a higher proportion of lysed red blood cells than a second canister exhibiting relatively greater haze around a similar edge, and Block S130 can thus select the algorithm, parametric model, or series of template images, accordingly.

Thus, once the algorithm, parametric model, or series of template images is selected in Block S130 based on the color gradient in the second region of the image, Block S140$b$ can pass a color parameter (e.g., redness value) of the first region of the image into the algorithm, parametric model, or series of template images to output an estimate of the hemoglobin concentration and/or the hemolysis status of hemoglobin contained in the canister.

Alternatively, Block S130 can extract a color parameter (e.g., a redness value) from the first region of the image—such as described in U.S. patent application Ser. No. 13/738,919—and select a particular algorithm, parametric model, or series of template images, etc. based on this color value. Block S140$b$ can then pass a metric derived from the color gradient into the selected algorithm, parametric model, or series of template images, etc. to output an estimate of the hemoglobin concentration and/or the hemolysis status of hemoglobin contained in the canister.

Yet alternatively, Block S130 can extract one or more quantitative values of the color gradient from the second region selected in Block S120, and Block S140$b$ can pass both a color value of the first region and the quantitative value(s) of the color gradient into a standardized parametric model to output an estimate of the hemoglobin concentration and/or the hemolysis status of hemoglobin contained in the canister.

However, Block S130 can function in any other way to extract relevant data from the color gradient in the second region of the image and/or to selecting a particular model, algorithm, or template image set suitable for estimating a quantity and/or quantity of hemoglobin in the canister.

5. Blood Component Concentration and Hemolysis Status

In relation to optional Blocks S120 and S130, Block S140b recites: estimating a concentration of a blood component and a hemolysis status of fluid within the canister based on a color in the first region of the image and the canister content model. Generally, Block S140b implements methods and techniques described in U.S. patent application Ser. No. 13/738,919 to correlate a color value in the image of the canister to a hemoglobin concentration (and/or a concentration of another blood component) in the canister. However, with the addition of a metric of light absorption (and/or opacity) of the fluid associated with a color gradient, Block S140b can further output a metric indicative of a quality of the hemoglobin (or other blood component) in the canister, based upon an estimation of hemolysis status.

In one implementation, Block S130 selects a generic multivariable parametric model, and Block S140b applies an average redness value in the red component space of the first region of the image and an absorption coefficient of the fluid and/or a coefficient of a line of best fit of the color gradient analyzed in Block S130 to a multivariable parametric model, in order to solve for a concentration of hemoglobin the canister and percentage of free hemoglobin (or a percentage of lysed red blood cells, a ratio of free hemoglobin to intracellular hemoglobin, etc.) in the canister.

Alternatively, Block S130 can select a particular set of template images—from a multitude of template images—of canisters containing fluids of known hemoglobin concentrations and hemolysis levels, and exhibiting substantially similar light absorption coefficients as the current canister. In this implementation, Block S140b can thus implement template matching to match the first region of the image to a particular template image of a template canister containing a volume of fluid of known hemoglobin concentration and hemolysis level. Block S140b can thus output the known hemoglobin concentration and hemolysis level of the template canister as an estimate of the hemoglobin concentration and hemolysis level of the current canister.

However, Blocks S110, S120, S130, and S140b can cooperate in any other suitable way to estimate the concentration of hemoglobin (and the hemolysis level) of the canister.

6. Additional Blood Component Values

As shown in FIGS. 1A and 1B, one variation of the method further includes Block S150, which recites: determining a volume of fluid within the canister, and Block S151, which recites: generating an analysis informative of an amount of the blood component within the canister, based upon the concentration of the blood component and the volume of fluid within the canister. In variations, Blocks S150 and S151 can include: within an image of a canister, identifying a reference marker on the canister, selecting an area of the image based on the reference marker, correlating a portion of the selected area with a fluid level within the canister, estimating a volume of fluid within the canister based on the fluid level, and estimating a mass of hemoglobin within the canister based on the estimated volume and the concentration of the hemoglobin in the canister. Generally, Block S150 can implement methods and techniques described in U.S. patent application Ser. No. 13/738,919 to detect the volume of fluid in the canister and to calculate the total volume, mass, weight, or other method of hemoglobin in the canister based on the total volume and the estimated blood component concentration in the canister.

Additionally or alternatively, Blocks S150 and S151 can include receiving information pertaining to the volume of fluid within the canister by an entity interacting with the system. In a first variation, the volume of fluid within the canister can be manually input (e.g., with keypad strokes, by speech, etc.) into an input module of a computing device of the system. In an example of the first variation, a holistic blood loss management application executing at a mobile computing device (e.g., tablet computer, smartphone device, etc.) can include a user interface configured to receive an input indicative of the volume of fluid within the canister, wherein the input is provided by a physician, nurse, assistant, or technician present within an operating room environment. In the example, the Block S150 can thus use the input volume of fluid information in estimating a quantity of the blood component within the canister. However, in alternative variations and examples, the quantity of the blood component within the canister can be determined in any other suitable manner.

Additionally or alternatively, Blocks S150 and S151 can implement methods and techniques described in U.S. patent application Ser. No. 14/072,625 to detect the volume of fluid in the canister and to calculate the total volume, mass, weight, or other method of the blood component in the canister based on the total volume and the estimated blood component concentration in the canister.

Blocks S150 and S151 can further combine an estimated hemolysis level in the canister with the estimated mass of hemoglobin in the canister to estimate a total mass of free hemoglobin and a total mass of intracellular hemoglobin in the canister, such as according to the formulas:

$$1 - \frac{V_{RBC} \cdot C_{RBC}}{V_{Hb_{free}} \cdot C_{Hb_{free}}} = 1 - \frac{m_{Hb_{RBC}}}{m_{Hb_{free}}} = \% \text{ Hemolysis}$$

$$V_{RBC} \cdot C_{RBC} = \frac{m_{Hb_{RBC}}}{\sim 0.35},$$

$$V_{fluid} \cdot C_{Hb_{total}} \cdot [\% \text{ Hemolysis}] = m_{Hb_{free}}$$

$$V_{fluid} \cdot C_{Hb_{total}} \cdot [1 - \% \text{ Hemolysis}] = m_{Hb_{RBC}}$$

$$m_{Hb_{RBC}} + m_{Hb_{free}} = m_{Hb_{total}}, \text{ and}$$

$$C_{Hb_{RBC}} + C_{Hb_{free}} = C_{Hb_{total}}.$$

Block S150 can then deliver prompts or other notifications to a user to salvage red blood cells from the canister if the amount of intra-cellular hemoglobin (or if the ratio of intra-cellular hemoglobin to free hemoglobin) exceeds a minimum threshold. Block S150 can similarly deliver a prompt to the user to not salvage red bloods cells from the canister if the amount of intra-cellular hemoglobin (or if the ratio of intra-cellular hemoglobin to free hemoglobin) falls short of the minimum threshold, such as described in U.S. patent application Ser. No. 14/072,625. Additionally or alternatively, outputs of Block S150 can be used to provide information pertaining to blood loss parameters of a patient to an entity (e.g., at an electronic computing device comprising a display configured to render the information).

The systems and methods of the preferred embodiment can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or mobile device, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention as defined in the following claims.

We claim:

1. A method for assessing an amount of a blood component of a volume of fluid within a canister, comprising:
    at a computing system in communication with an image acquisition device, receiving data associated with an image of the canister generated by the image acquisition device;
    at the computing system, automatically selecting a first region of the image corresponding to a layer of fluid situated between a wall of the canister and a first feature of an insert retained in a first position within the canister that is offset from the wall of the canister;
    at the computing system, determining a color parameter representative of the first region of the image;
    at the computing system, determining a concentration of a blood component within the canister, based upon the color parameter;
    upon determining the volume of fluid within the canister, generating an analysis informative of an amount of the blood component within the canister; and
    at an output device in communication with the computing system, providing information derived from the analysis to an entity associated with an individual from whom the volume of fluid originated.

2. The method of claim 1, further comprising retaining the insert within the container prior to receiving fluid from the patient in the canister.

3. The method of claim 2, wherein retaining the insert within the canister comprises providing alignment between the first feature of the insert and an anti-glare layer of a color grid coupled to an external surface of the canister.

4. The method of claim 1, further comprising determining the volume of fluid within the canister by performing at least one of: 1) receiving information pertaining to the volume of fluid within the canister at an input device in communication with the computing system, and 2) identifying a reference marker on the canister, selecting an area of the image based upon the reference marker, determining a fluid level within the canister based upon a portion of the area, and estimating the volume of fluid within the canister based upon the fluid level.

5. The method of claim 1, further comprising: at the computing system, automatically selecting a second region of the image exhibiting a color gradient, and determining at least one of the concentration of the blood component within the canister and a hemolysis status of fluid within the canister based upon the second region of the image.

6. The method of claim 5, wherein selecting the second region of the image exhibiting the color gradient comprises transmitting light, from a light source, through fluid within the canister, thereby inducing the color gradient.

7. The method of claim 6, wherein transmitting light comprises transmitting light from a light source coupled to the insert.

8. The method of claim 6, wherein transmitting light comprises transmitting light characterized by at least one wavelength between one or more of: 400-700 nm and 800-950 nm, in relation to hemoglobin light absorption, and wherein determining the hemolysis status is based upon signals generated by an image acquisition device external to the canister.

9. The method of claim 5, further comprising retaining a second feature of the insert in a second position such that the second feature provides a region with a gradient in fluid thickness between the second feature and wall of the canister.

10. The method of claim 9, wherein the second feature comprises a set of first features arranged in a stepped configuration, each of the set of first features offset from the wall of the canister, and wherein the method further comprises: generating a parameter from each of the set of features; classifying fluid according to a concentration regime of a set of concentration regimes based upon the parameters generated from the set of first features; and determining the concentration of the blood component within the canister based upon the concentration regime.

11. A system for assessing an concentration of a fluid component, the system comprising:
    a container for receiving a volume of fluid from a patient;
    an insert configured to be retained within the container such that a first feature of the insert is offset from a wall of the container; and
    a computing system in communication with an image acquisition device and comprising:
        a first module configured to receive an image dataset of the container generated by the image acquisition device;
        a second module configured to automatically select a first region of the image corresponding to fluid between the wall of the container and the first feature of the insert;
        a third module configured to determine a parameter representative of the first region of the image; and
        a fourth module configured to determine a concentration of a fluid component within the container, based upon the parameter.

12. The system of claim 11, further comprising an output device in communication with the computing system, and configured to render information derived from the analysis to an entity associated with an individual from whom the volume of fluid originated, wherein the output device is integrated with the image acquisition device.

13. The system of claim 11, wherein the insert includes an alignment feature that couples the insert to the container.

14. The system of claim 13, wherein the insert includes a cylindrical base at an inferior end of the insert and a frustoconical portion superior to the cylindrical base, wherein the cylindrical base defines the first feature and wherein the frustoconical portion defines a second feature configured to provide a color gradient upon reception of fluid into the container.

15. The system of claim 13, wherein the insert includes a set of first features arranged in a stepped configuration, each of the set of first features offset from the wall of the container and from an adjacent first feature.

16. The system of claim 15, wherein the third module of the computing system is configured to generate a parameter from each of the set of first features; classify fluid according to a concentration regime of a set of concentration regimes based upon the parameters generated from the set of first features; and determine the concentration of the fluid component within the container based upon the concentration regime.

17. The system of claim 11, further comprising an illumination module in communication with the container, wherein the illumination module is configured to transmit light through fluid within the container.

18. The system of claim 17, wherein the illumination module comprises a light source configured to transmit light characterized by at least one wavelength between one or more of: 400-700 nm and 800-950 nm, in relation to hemoglobin light absorption.

19. The system of claim 17, wherein the illumination module is coupled to the insert retained within the container.

20. The system of claim 11, further comprising a fifth module configured to determine a volume of fluid within the container upon at least one of: receiving information pertaining to the volume of fluid within the canister at an input device in communication with the computing system, and 2) identifying a reference marker on the container, selecting an area of the image based upon the reference marker, determining a fluid level within the container based upon a portion of the area, and estimating the volume of fluid within the container based upon the fluid level.

21. The method of claim 1, wherein the first region of the image exhibits a substantially uniform color.

22. The system of claim 11, wherein the first region of the image exhibits substantially uniform characteristics.

* * * * *